US006409664B1

(12) United States Patent
Kattan et al.

(10) Patent No.: US 6,409,664 B1
(45) Date of Patent: *Jun. 25, 2002

(54) NOMOGRAMS TO AID IN THE TREATMENT OF PROSTATIC CANCER

(76) Inventors: Michael W. Kattan, 504 E. 63rd St., Apt. 20P; Peter T. Scardino, 345 E. 68th St., Apt 2B, both of New York, NY (US) 10021

( * ) Notice: Subject to any disclaimer, the term of this patent is extended or adjusted under 35 U.S.C. 154(b) by 0 days.

This patent is subject to a terminal disclaimer.

(21) Appl. No.: 09/444,706

(22) Filed: Nov. 24, 1999

Related U.S. Application Data

(63) Continuation of application No. 09/104,218, filed on Jun. 25, 1998, now Pat. No. 5,993,388.
(60) Provisional application No. 60/051,478, filed on Jul. 1, 1997.

(51) Int. Cl.[7] ............................ A61B 5/00; A61B 19/00

(52) U.S. Cl. ........................................ 600/300; 128/898
(58) Field of Search ............................... 600/300; 435/6

(56) References Cited

U.S. PATENT DOCUMENTS

| 5,733,721 A | * | 3/1998 | Hemstreet, III et al. ......... 435/6 |
| 5,945,289 A | * | 8/1999 | Lehrer ............................. 435/6 |
| 5,993,388 A | * | 11/1999 | Kattan et al. ................ 600/300 |
| 6,004,267 A | * | 12/1999 | Tewari et al. ................ 600/300 |

OTHER PUBLICATIONS

Chodak, et al., "Results of Conservative Management of Clinically Localized Prostate Cancer", *N. Engl. J. Med.* 1994; 330:242–248.

Albertson, et al., "Long–term Survival Among Men With Conservatively Treated Localized Prostate Cancer", *JAMA* 1995; 274:626–631.

Hanks, et al., "Clinical and Biochemical Evidence of Control of Prostate Cancer at 5 Years After External Beam Radiation", *J. Urol* 1995; 154:456–9.

Bagshaw, et al. "Control of Prostate Cancer with Radiotherapy: Long–Term Results",*J. Urol.,*1994; 152:1781–5.

Ohori, et al., "Prognostic Significance of Positive Surgical Margins in Radical Prostatectomy Specimens", *J. Urol.,* 1995; 154:1818–24.

Gerber, et al., "Results of Radical Prostatectomy in Men with Clinically Localized Prostate Cancer", *JAMA* 1996; 276:615–9.

Pound, et al, "Prostate–Specific Antigen After Anatomic Radical Retropubic Prostatectomy", Urol. Clin. North Am. 1997; 24:395–406.

Trapasso, et al., "The Incidence and Significance of Detectable Lvels of Serum Prostate Specific Antigen After Radical Prostatectomy", *J. Urol.* 1994; 152:1821–5.

Ohori, et al., "The New American Joint Committee on Cancer and International Union Against Cancer TNM Classification of Prostate Cancer", *Cancer* 1994; 73:1904–12.

Zagars, et al., "The T Classification of Clinically Localized Prostate Cancer", *Cancer* 1994; 73:1904–12.

Rogers, et al., "Salvage Radical Prostatectomy: Outcome Measured by Serum Prostate Specific Antigen Levels", *J. Urol.* 1995; 153:104–10.

Harrell, F., Transcan: an S–Plus Function (program available from statlib@lib.stat.cmu.edu).

(List continued on next page.)

Primary Examiner—Eric F. Winakur
(74) Attorney, Agent, or Firm—Heller Ehrman White McAuliffe

(57) ABSTRACT

This invention relates to methods and apparatus for predicting probability of cancer recurrence following radical prostatectomy using predetermined clinical and pathological factors. The invention includes nomograms which can be used preoperatively and postoperatively in patients diagnosed with prostatic adenocarcinoma to aid in selection of an appropriate course of therapy.

64 Claims, 9 Drawing Sheets

OTHER PUBLICATIONS

Harrell, et al., "Tutorial in Biostatistics: Multivariable Prognostic Models: Issues in Developing Models, Evaluating Assumptions and Adequacy, and Measuring and Reducing Errors", *Stats Med* 1996; 15:361–387.

Hanley, et al., "The Meaning and Use of the Area Under a Receiver Operating Characteristic (ROC) Curve", *Radiology* 1982; 143:29–36.

Harrell, F., "Design: S–Plus function for biostatiscal/epidemiologic modeling, testing, estimation, validation, graphics, predication, and typesetting by storing enhanced model design attributes in the fit", 1994 (program available from statlib@lib.stat.cmu.edu).

Dillioglugil et al., "Hazard Rates for Progression After Radical Prostatectomy for Clinical Localized Prostate Cancer", *Urol* 1997; 50(1):93–9.

Kattan et al., "Evaluation of a Nomogram Used to Predict the Pathologic Stage of Clinically Localized Prostate Carcinoma", *Cancer* 1997; 79(3):528–537.

Carter, et al., "The Use of Prostate Specific Antigen in the Management of Patients with Prostate Cancer", *Clinical Aspects of Prostrate Cancer*, New York: Elsevier Science Publishing, 1989:247–54.

Partin, et al., "Serum PSA After Anatomic Radical Prostatectomy: The Johns Hopkins Experience After 10 Years", *Urol Clin North Am* 1993; 20(4):713–725.

Epstein, et al., "Correlation of Pathologic Findings with Progression after Radical Retropublic Prostatectomy", *Cancer* 1993; 71:3582–3593.

Stein, et al., "Prostate Specific Antigen Levels After Radical Prostatectomy in Patient with Organ Confinded and Locally Extensive Prostate Cancer", *J Urol* 1992; 147:942–6.

Dorey, et al., "Multiple Imputation for Theshold–Crossing Data with Interval Censoring", *Stats in Med* 1993; 12:1589–1603.

D'Amico, et al., "A Multivariate Analysis of Clinical and Pathological Factors that Predict for Prostate Specific Antigen Failure After Radical Prostatectomy for Prostate Cancer", *J Urol* 1995; 154:131–138.

Partin, et al., "Selection of Men at High Risk for Disease Recurrance for Experimental Adjuvant Therapy Following Radical Prostatectomy", *Urology* 1995; 45:831–838.

Kupelian, et al., "External Beam Radiotheraphy versus Radical Prostatectomy for Clinical Stage T1–2 Prostate Cancer: Therapeutic Implications of Stratification by Pretreatment SA Levels and Biopsy Gleason Scores", *Cancer J Sci Amer* 1997; 3(2):78–87.

Stamey, et al., "Positive Surgical Margins at Radical Prostatectomy: Inportance of the Apical Dissection", *J Urol* 1990: 143:1166–1173.

Kattan, et al., "A Decision Analysis for Treatment of Clinically Localized Prostate Cancer", *J Gen Intern Med* 1997; 12:299–305.

Partin, et al., "The Use of Prostate Specific Antigen, Clinical Stage and Gleason Score to Predict Pathological Stage in Men With Localized Prostate Cancer", *J. Urol* 1993; 150:110–114.

Partin, et al., "Combination of Prostate–Specific Antigen, Clinical Stage, and Gleason Score to Predict Pathological Stage of Localized Prostate Cancer", *JAMA* 1997; 277(18):1445–1451.

Badalament, et al., "Algorithm for Predicting Nonorgan Confined Prostate Cancer Using the Results Obtained from Sextant Core Biopsies with Prostate Specific Antigen Level", *J Urol* 1996; 156:1375–1380.

Narayan, et al., "The Role of Transrectal Ultrasound–Guided Biopsy–Based Staging, Preoperative Serum Prostate–Specific Antigen, and Biopsy Gleason Score in Prediction of Final Pathologic Diagnosis in Prostate Cancer", *Urology* 1995; 46(2):205–212.

Bostwick, et al., "Optimized Microvessel Density Analysis Improved Prediction of Cancer Stage from Prostate Needle Biopsies", *Urology* 1996; 48(1): 47–57.

Bauer, et al., "Biostatistical modeling Using Traditional Preoperative and Pathological Prognostic Variables in the Selection of Men at High Risk for Disease Recurrence After Radical Prostatectomy for Prostate Cancer", *J Urol* 1998; 159:929–933.

Knaus, et al., "Short–Term Mortality Predictions for Critically Ill Hospitalized Adults: Science and Ethics", *Science* 1991; 254:389–394.

Bauer, et al., "Biostatistical Modeling Using Traditional Variables and Genetic Biomarkers for Predicting the Risk of Prostate Carcinoma Recurrence after Radical Prostatectomy", *Cancer* 1997; 79(5):952–962.

Gleason, D., *Urologic Pathology: The Prostate*, "Histologic Grading and Clinical Staging of Prostatic Carcinoma", Lea and Febiger, Philadelphia, 1977, pp. 171–197.

Schroder, et al., "The TNM Classification of Prostate Cancer", *Pros Supp* 1992; 4:129–138.

Cox, D., "Regression Models and Life Tables", *J Royal Stat Soc,* 1972.

Rumelhart, et al., *"Parallel Distributed Processing: Explorations in the Microstructure of Cognition, vol. 1: Foundations"*, Cambridge, MA, The MIT Press 1986.

Breiman et al., *"Classification and Regression Trees"*, Monterey, CA, Wadsworth and Brooks/Cole 1984.

Goto, et al., "Distinguishing Clinically Important From Unimportant Prostate Cancers Before Treatment: Value of Systematic Biopsies", *J Urol* 1996; 156:1059–1063.

Stapleton, et al., "Assessment of the Biologic Markers p53, Ki–67, and Apoptotic Index as Predictive Indicators of Prostate Carcinoma Recurrence after Surgery", *Cancer* 1998; 82(1):168–75.

Stapleton, et al., "Assessment of the Biologic Markers of p53, Ki–67, and Apoptotic Index as Predictive Indicators of Prostate Carcinoma Recurrence after Surgery", *Cancer* 1998; 82(1):168–75.

Yang, et al., "Low P27 Expression Predicts Poor Disease–Free Survival with Prostate Cancer", *J Urol* 1998; 159:941–945.

Sridhara, et al., "Evaluation of Prostate–Specific Antigen as a Surrogate Marker for Response of Hormone–Refractory Prostate Cancer to Suramin Therapy", *J Clin Oncol* 1995; 13(12):2944–2953.

Moul, et al., "Black Race is an Adverse Prognostic Factor for Prostate Cancer Recurrence Following Radical Prostatectomy in An Equal Access Health Care Setting", *J Urol* 1996; 155:1667–1673.

Wheeler, T., "Anatomic Consideration s in Carcinoma of the Prostate", *Urol Clinics of N Amer* 1989; 16(4):623–634.

Rice, et al., "Granulomatous Infections Complicating Hairy Cell Leukemia", *Cancer* 1982; 49(2):1924–1928.

Ohori, et al., "The Mechanisms and Prognostic Significance of Seminal Vesicle Involvement by Prostate Cancer", *Amer J Surg Path* 1993; 17(12):1252–1261.

Efron, et al., "An Introduction to the Bootstrap", New York, NY, Chapman and Hall, 1993.

Califf, et al., "Selection of Thrombolytic Therapy for Individual Patients: Development of a Clinical Model", *Amer Heart J* 1992; 133(6):630–639.

Knaus, et al., "The Clinical Evaluation of New Drugs for Sepsis: A Prospective Study Design Based on Survival Analysis", *JAMA* 1993; 270(10):1233–1241.

Knaus, et al., "What determines prognosis in sepsis? Evidence for a comprehensive individual patient risk assessment approach to the design and analysis of clinical trials", *Theor Surg* 1994; 9:20–27.

Knaus, et al., "Use of Predicted Risk of Mortality to Evaluate the Efficacy of Anticytokine Therapy in Sepsis", *Crit Care Med* 1996; 24(1): 46–56.

Greene, et al., "A Comparison of the Morphological Features of Cancer Arising in the Transition Zone and in the Peripheral Zone of the Prostate", *J Urol* 1991; 146:1069–1076.

Greene, et al., *Campbell's Urology*, vol. 1, 6th Ed., W.B. Saunders Co., 1992.

Ohori et al., "Comparison of the Pathologic Features and DNA Ploidy Value of Prostate Cancers Detectable by Sonography and by Palpation", *Prostate* 1993; 23(4):271–281.

Stamey et al., "Morphometric and Clinical Studies on 68 Consecutive Radical Prostatectomies", *J Urol* 1988;139:1235–1241.

Rosen, et al., "Frequency and Location of Extracapsular Extension and Positive Surgical Margins in Radical Prostatectomy Specimens", *J Urol* 1992; 148:331–337.

Wheeler, et al., "Clinical and Pathological Significance of the Level and Extent of Capsular Invasion in Clinical Stage T1–2 Prostate Cancer", *Hum Path* 1998; 29(8):856–862.

Greene, et al., "Relationship between Clinical Stage and Histological Zone of Origin in Early Prostate Cancer: Morphometric Analysis", *J Urol* 1991; 68:499–509.

Harrell, F., "Predicting Outcomes: Applied Survival Analysis and Logistic Regression", Chap. 7, *Cox Proportional Hazards Regression Model;* 1997.

Kattan, et al., "Development of a Nomogram Using Clinical (Preoperative) Factors to Predict Progression After Radical Prostatectomy for Prostate Cancer", J. Urol. AUA Ninety-Second Annual Meeting, Apr.12–17, 1997 (abstract No. 1161).

Kattan, M., "Nomogram Development and Its Use in Prostate Cancer", Presentation at the 4th Innovations in Urologic Practice, Jan. 31, 1997–Feb. 2, 1997.

* cited by examiner

NOMOGRAMS TO AID IN THE TREATMENT OF PROSTATIC CANCER

REFERENCE TO RELATED APPLICATIONS

This patent application is a Continuation of co-pending U.S. patent application Ser. No. 09/104,218, filed Jun. 25, 1998, which claims priority under 35 U.S.C. § 119(e), on U.S. Provisional application Ser. No. 60/051,428, filed Jul. 1, 1997.

BACKGROUND OF THE INVENTION

1. Field of the Invention

This invention relates to methods and apparatuses for predicting probability of disease recurrence following radical prostatectomy using predetermined clinical and pathological factors. The invention includes nomograms that can be used preoperatively and postoperatively to aid in selection of an appropriate course of therapy.

2. Description of Background

Prostate adenocarcinoma is the most common malignancy in males over the age of 50. Clinically localized prostate cancer is most often treated with conservative management (G. W. Chodak et al., N. Engl. J. Med. 330:242–248, 1994; P. C. Albertson et al., JAMA 274:626–63, 1995), external beam irradiation (G. E. Hanks et al., J. Urol. 154:456–9, 1995; M. A. Bagshaw et al., J Urol 152:1781–5, 1994), or radical prostatectomy (M. Ohori et al., J. Urol. 154:1818–24, 1995; G. S. Gerber et al., JAMA 276:615–9, 1996; C. R. Pound et al., Urol. Clin. North Am. 24:395–406, 1997; J. G. Trapasso et al., J Urol 152:1821–5, 1996), and occasionally with therapeutic interventions such as interstitial radioactive seed implantation or cryotherapy. Making a decision among the different management choices for clinically localized prostate cancer would be greatly facilitated if reliable predictors of the probability that the selected treatment would control the cancer long term were available. Currently, there are no satisfactory randomized prospective trials comparing cancer control among alternative treatments. Although clinical trials are underway, even when these trials are completed, all patients with a clinically localized cancer will not have an equal probability of a successful outcome.

a. Preoperative Assessment

Prior to undergoing radical prostatectomy, it is of great interest to the patient to know whether the procedure is likely to be curative. Because the pathologic stage of cancer correlates with the probability of recurrence after surgery, a number of investigators have made efforts based on cohort studies to predict the final pathologic stage of prostate cancer using various parameters. A number of nomograms and algorithms have been formulated in an effort to identify the pathological stage of an individual's prostatic cancer. For instance, Partin, et al., has developed a nomogram based on pretreatment prostate specific antigen level (PSA), tumor grade, and clinical stage, to aid physicians in making treatment recommendations by predicting the probability of the final pathological stage of clinically localized prostate carcinoma. (A. W. Partin et al., J. Urol. 115:110–4, 1993). This nomogram was based on data for one patient population. However, although this nomogram does discriminate between organ-confined and non-confined cancer, it has difficulty predicting high probabilities of seminal vesicle invasion and lymph node metastasis, which are the pathologic features with the most profound impact on prognosis. (M. Kattan et al., Cancer 79:528–537, 1997). In addition, this type of nomogram, including the updated version (Partin et al., JAMA 277:1445–1451, 1997), does not provide the physician with a simple means of advising a patient of the likelihood of recurrence if a radical prostatectomy is performed.

Another algorithm developed pursuant to a study by Badalament et al., purports to predict non-organ confined prostate cancer. This study found that nuclear grade, preoperative PSA, total percent tumor involvement, number of positive sextant cores, preoperative Gleason score, and involvement of more than five percent of abase and/or apex biopsy were significant for prediction of disease organ confinement status. (R. Badalament et al., J. Urol. 156:1375–1380, 1996).

Another predictor by Narayan et al., uses preoperative serum PSA, biopsy Gleason score, and biopsy-based stage to predict final pathological stage, by constructing probability plots. (P. Narayan et al., Urology 46:205–212,1995). Yet another predictor by Bostwick et al., uses PSA concentrations, optimized microvessel density of needle biopsy samples and Gleason score to predict extra-prostatic extension. (David Bostwick et al., Urology 48:47–57, 1996).

Existing preoperative predictors typically use final pathologic stage as their end point. (A. W. Partin et al., JAMA 277:1445–1451, 1997). This point is problematic in that some patients with apparently organ confined disease will later develop disease recurrence, whereas many patients with non-organ confined disease will remain disease free. (M. W. Kattan et al., Cancer 793:528–537, 1997). Extracapsular tumor extension, positive surgical margins, seminal vesicle involvement and positive pelvic lymph nodes are adverse pathological features. (A. W. Partin et al., Urol. Clin. North Am. 204:713–725, 1993; J. I. Epstein et al., Cancer 71:3582–3593, 1993; A. Stein et al., J. Urol. 147:942, 1992). Yet not all patients with one or more of these findings are destined to have disease recurrence after radical prostatectomy. Of the 462 men evaluated by Partin et al. with either focal or established extracapsular penetration (A. W. Partin et al., Urol. Clin. North Am. 20(4):713–725, 1993), only 80 (17%) had evidence of disease recurrence with a mean follow-up of 53 months (range 12 to 120 months). Similarly, Ohori and colleagues report a five-year PSA progression rate of 25% for patients with extracapsular extension in the radical prostatectomy specimen. (M. Ohori et al., Cancer 74:104–14, 1994). In a study of the association between positive surgical margins and disease progression, Epstein et al. found that only half of their patients with positive margins developed disease recurrence. (J. I. Epstein et al., Cancer 71:3582–3593, 1993). Thus, using final pathologic stage as an end point limits the utility of a nomogram to accurately predict disease recurrence following radical prostatectomy. In addition, although final pathology has been associated with eventual treatment failure, none of the existing predictors allow the physician to accurately predict preoperatively the likelihood of recurrence of cancer in a patient if a radical prostatectomy is performed. This is typically the information of greatest interest to the patient before electing to undergo surgery.

There are several established prognostic factors relating to the risk of recurrence after surgery or radiotherapy or the risk of metastasis or death from cancer after conservative management, including clinical stage (M. Ohori et al., Cancer 74:104–14, 1994), Gleason grade (P. C. Albertson et al., JAMA 274:626–631, 1995; G. E. Hanks et al., J. Urol. 154:456–9, 1995; G. S. Gerber et al., JAMA 276:615–9, 1996) and serum prostate specific antigen (PSA) levels (G. K. Zagars, Cancer 73:1904–12; 1994). Prior to the present invention, these three routinely available prognostic factors had not been successfully combined into a risk profile that could be used to predict, prior to surgery, the probability of recurrence or metastatic progression after surgical management.

b. Post-Operative Assessment

The most common aggressive therapy for the treatment of clinically localized prostate cancer is radical prostatectomy. Unfortunately, approximately one third of men treated with radical prostatectomy later experience progression of their disease. Typically, the first indication that the disease has progressed occurs as a detectable level of serum PSA months or years following surgery. Early identification, prior to detectable PSA, of men likely to ultimately experience progression would be useful in considering adjuvant therapy or, before documented progression, when adjuvant therapy may be most effective. Accurate identification of the probability of recurrence would also be particularly useful in clinical trials to assure comparability of treatment and control groups or to identify appropriate candidates for investigational treatment such as gene therapy.

Traditionally, the judgment of which patients are at high risk for failure following radical prostatectomy has been based largely on final pathologic stage. As noted, final pathologic stage alone (A. W. Partin et al., JAMA 277:1445–1451, 1997) is a problematic variable for judging high-risk disease since some patients with apparently organ-confined cancer will later develop disease recurrence, and many patients with non-organ-confined cancer will remain disease-free (C. R. Pound et al., Urol. Clin. North Am. 24:395–406, 1997). Not all patients with extracapsular extension or seminal vesicle involvement are destined to have disease recurrence after radical prostatectomy (M. Ohori et al., Cancer 74:104–14, 1994; M. Ohori et al., J. Urol. 154:1818–1824, 1995; C. R. Pound et al., Urol. Clin. North Am. 24:395–406,1997; J. G. Trapasso et al., J. Urol. 152:1821–1825, 1994; A. W. Partin et al., Urol. Clin. North Am. 20:713–725, 1993; J. I. Epstein et al., Cancer 71:3582–3593, 1993). Thus, the use of individual pathologic features appears insufficient to estimate probability for recurrence; a method of combining them is needed.

In 1995, Partin and colleagues (A. W. Partin et al., Urology 45:831–838,1995) published a model for predicting relative risk that was derived using 216 men with clinical stage T2b and T2c prostate cancer treated by a single urologist. The model utilized pretreatment serum PSA with a sigmoidal transformation, radical prostatectomy Gleason score (Gleason sum), and pathologic stage as specimen confined or nonspecimen confined to identify patients with a high relative risk of recurrence following surgery. Their model computed log relative risk and categorized patients into low, intermediate, and high. In a validation cohort of 214 patients treated by one of three different urologists at two institutions, Partin was able to illustrate that the model was apparently able to stratify those patients as well, based on their Kaplan-Meier PSA recurrence-free survival rates although no statistical testing of strata differences was performed. Bauer et al. (J. J. Bauer et al., J. Urol. 159:929–933, 1998) recently emulated Partin's approach with 378 patients but added race as a predictor variable and widened the cohort to include all clinical stages up to T1a through T2c. Another difference with the Bauer model was the cutoffs used to distinguish the risk groups (relative risks of 4.0 and 5.75 for Partin versus 10 and 30 for Bauer). Bauer's validation cohort of 99 men indicated a difference in survival rates between the low- and high-risk groups but no difference between intermediate risk and either low or high risk. In another recent study, Bauer (J. J. Bauer et al., Cancer 79(5):952–962, 1997) added biomarkers p53, Ki-67, and bcl-2 to the relative risk calculation. Finally, Harrell et al., discloses a nomogram which evaluates estrogen as a treatment for prostate cancer. This nomogram uses numerous variables, such as age, weight index, blood pressure data, history of cardiovascular disease, tumor size, tumor grade and serum prostatic acid phosphatase to predict survival. (F. Harrell et al., Statistics in Medicine 15:361–387, 1996).

However, none of the postoperative models currently available predict probability of recurrence. Moreover, prior to the present invention, there has been no method or means to predict the probability of treatment failure following surgery, defined as a rising PSA level, following radical prostatectomy for clinically localized prostate cancer. Such risk profiles would be very useful in providing meaningful information to a patient making a decision among courses of therapy. Such a tool would provide the patient with his probability of recurrence instead of a relative risk which is more easily comprehended. While the relative risk informs the patient of his risk of recurring relative to another patient with certain characteristics, the actual probability should more greatly facilitate decision making for the patient.

SUMMARY OF THE INVENTION

Therefore, a need has arisen for a method and apparatus to accurately predict prior to surgery the likelihood of recurrence in an individual diagnosed with prostate cancer following radical prostatectomy, using routinely available clinical variables. In addition, a need has arisen for a method and apparatus for accurately predicting probability of recurrence post-prostatectomy, using data collected and available immediately postoperatively, to evaluate whether adjuvant therapy may be warranted before PSA begins to rise.

The present invention is directed to methods and apparatuses for predicting probability of disease recurrence following radical prostatectomy using routinely performed and available factors. The invention includes nomograms that can be used preoperatively and postoperatively to aid in selection of an appropriate course or courses of therapy.

One embodiment of the invention is directed to a method for predicting probability of recurrence of prostatic cancer following radical prostatectomy in a patient diagnosed as having prostatic cancer. This method comprises the steps of correlating a selected set of preoperative factors determined for each of a plurality of persons previously diagnosed with prostatic cancer and having been treated by radical prostatectomy with the incidence of recurrence of prostatic cancer for each person of said plurality of persons to generate a functional representation of the correlation, wherein said selected set of preoperative factors comprises pretreatment PSA level, combined Gleason grade in the biopsy specimen and clinical stage, and matching an identical set of preoperative factors determined from the patient diagnosed as having prostatic cancer to the functional representation to predict the probability of recurrence of prostatic cancer in the patient following radical prostatectomy. In another embodiment, biopsy Gleason sum may be used instead of combined Gleason grade. In another embodiment, the factors may further comprise one or more of the following: total length of cancer in the biopsy cores; maximum cancer length in a core; and apoptotic index.

Another embodiment of the invention is directed to a postoperative method for predicting probability of recurrence of prostatic cancer in a patient who has previously undergone a radical prostatectomy. This method comprises the steps of correlating a selected set of factors determined for each of a plurality of persons previously diagnosed with prostatic cancer with the incidence of recurrence of prostatic cancer for each person of said plurality to generate a functional representation of the correlation, wherein said selected set of factors comprises preoperative PSA level, specimen Gleason sum, prostatic capsular invasion level, surgical margin status, presence of seminal vesicle invasion, and lymph node status, wherein said plurality of persons comprises men having undergone radical prostatectomy, and matching an identical set of factors determined from the patient to the functional representation to predict the probability of recurrence of prostatic cancer for the patient.

Additional embodiments of the invention are directed to nomograms for determining a preoperative probability of prostatic cancer recurrence such as those depicted in FIGS. 2A and 2B and methods of using these nomograms to predict a patient's prognosis. One such method predicts a patient's preoperative prognosis by matching a patient-specific set of preoperative factors comprising pretreatment PSA level, clinical stage, and combined Gleason grade to the nomogram depicted in FIG. 2A or FIG. 2B and determining the preoperative prognosis of the patient.

Additional embodiments of the invention are directed to a nomogram for determining a postoperative probability of prostatic cancer recurrence such as depicted in FIG. 5 and methods of using this nomogram to predict a patient's prognosis. One such method predicts a patient's postoperative prognosis following radical prostatectomy by matching a patient-specific set of factors comprising the patient's preoperative PSA level, specimen Gleason sum, prostatic capsular invasion level, surgical margin status, presence of seminal vesicle invasion, and lymph node status to the nomogram depicted in FIG. 5 and determining the prognosis of the patient.

Another embodiment of the invention is directed to a method for determining a need for an adjuvant therapy in a patient following radical prostatectomy comprising the steps of determining a set of factors on the patient, the set of factors comprising the patient's preoperative PSA level, specimen Gleason sum, prostatic capsular invasion level, surgical margin status, presence of seminal vesicle invasion, and lymph node status; and matching the set of factors to the nomogram depicted in FIG. 5 to determine whether the adjuvant therapy is needed in view of the probability of recurrence.

Another embodiment of the invention is directed to an apparatus for predicting probability of disease recurrence in a patient with prostatic cancer following a radical prostatectomy, wherein the apparatus comprises a correlation of preoperative factors determined for each of a plurality of persons previously diagnosed with prostatic cancer and having been treated by radical prostatectomy with incidence of recurrence of prostatic cancer for each person of said plurality of persons, wherein said selected set of preoperative factors comprises pretreatment PSA level, combined Gleason grade in the biopsy specimen and clinical stage; and a means for matching an identical set of preoperative factors determined from the patient diagnosed as having prostatic cancer to the correlation to predict the probability of recurrence of prostatic cancer in the patient following radical prostatectomy.

Another embodiment of the invention is directed to an apparatus for predicting probability of disease recurrence in a patient with prostatic cancer following a radical prostatectomy, wherein the apparatus comprises: a correlation of clinical and pathological factors determined for each of a plurality of persons previously diagnosed with prostatic cancer and having been treated by radical prostatectomy with incidence of recurrence of prostatic cancer for each person of said plurality of persons wherein said selected set of factors comprises preoperative PSA level, specimen Gleason sum, prostatic capsular invasion level, surgical margin status, presence of seminal vesicle invasion, and lymph node status; and a means for matching an identical set of factors determined from the patient diagnosed as having prostatic cancer to the correlation to predict the probability of recurrence of prostatic cancer in the patient following radical prostatectomy.

Still another embodiment of the invention is directed to a nomogram for the graphic representation of the probability that a patient with prostate cancer will remain free of disease following radical prostatectomy comprising a substrate or a solid support and a set of indicia on the substrate or solid support, the indicia comprising a pretreatment PSA level line, a clinical stage line, a combined Gleason grade line, a points line, a total points line and a predictor line, wherein said pretreatment PSA level line, clinical stage line and combined Gleason grade line each have values on a scale which can be correlated with values on a scale on the points line, and wherein said total points line has values on a scale which may be correlated with values on a scale on the predictor line, such that the value of each of the points correlating with the patient's pretreatment PSA level, combined Gleason grade, and clinical stage can be added together to yield a total points value, and the total points value may be correlated with the predictor line to predict the probability of recurrence.

Still another embodiment of the invention is directed to a nomogram for the graphic representation of the probability that a patient with prostate cancer will remain free of disease following radical prostatectomy comprising a substrate or solid support and a set of indicia on the substrate or solid support, the indicia comprising a preoperative PSA level line, a specimen Gleason sum line, a prostatic capsular invasion level line, a surgical margin status line, a presence of seminal vesicle invasion line, a lymph node status line, a points line, a total points line and a predictor line, wherein said preoperative PSA level line, specimen Gleason sum line, prostatic capsular invasion level line, surgical margin status line, presence of seminal vesicle invasion line, and lymph node status line each have values on a scale which can be correlated with values on a scale on the points line, and wherein said total points line has values on a scale which may be correlated with values on a scale on the predictor line, such that the value of each of the points correlating with the patient's preoperative PSA level, specimen Gleason sum, prostatic capsular invasion level, surgical margin status, presence of seminal vesicle invasion, and lymph node status can be added together to yield a total points value, and the total points value can be correlated with the predictor line to predict the probability of recurrence.

As will be clear to those of skill in the art, the present invention may be modified to incorporate additional or fewer clinical, pathological and other variables. The invention may also be modified so as to allow prediction of the probability of recurrence after a variety of one or more therapies. As will further be clear to those of skill in the art, the invention may be embodied in any desired computerized format, including, but not limited to, those formats discussed below.

A further embodiment of the invention is directed to an apparatus for predicting a quantitative probability of disease recurrence in a patient with prostatic cancer following an identified therapy, in which the apparatus comprises a correlation of factors determined for each of a plurality of persons previously diagnosed with prostatic cancer and having been treated by the identified therapy with incidence of recurrence of prostatic cancer for each person of the plurality of persons. The apparatus further comprises a means for comparing an identical set of factors determined from the patient diagnosed as having prostatic cancer to the correlation to predict the quantitative probability of recurrence of prostatic cancer in the patient following the identified therapy. Preferably, the selected set of factors comprises two or more factors selected from the group consisting of pretreatment PSA level, combined Gleason grade, specimen Gleason sum, clinical stage, surgical margin status, prostatic capsular invasion level, extraprostatic extension, level of extraprostatic extension, apoptotic index, maximum cancer length in a core, total length of cancer in the biopsy cores, percent of cores positive, percent of cancer in one or more cores, percent of high grade cancer in one or more cores, total tumor volume, zone of location of the cancer, presence of seminal vesicle invasion, type of seminal vesicle invasion, p53, Ki-67, p27, DNA ploidy status, lymph node status, and lymphovascular invasion. Identified therapies include, but are not limited to, radical prostatectomy, radiation therapy, brachytherapy, hormonal therapy, cryotherapy, chemotherapy and combinations thereof.

The apparatus may assume a computerized or non-computerized form. For example, the apparatus may comprise a nomogram. In still another embodiment, the nomogram comprises a graphic representation which is disposed on a laminated card or other substrate. Alternately, the nomogram may be computerized and stored in a memory. Useful memory formats include, but are not limited to, random access memory, read-only memory, disk, virtual memory, processors, and the like. The nomogram may be stored in a database and may be accessible by multiple users.

The apparatus may further comprise a display that displays the quantitive probability of recurrence of prostatic cancer. The display may comprise a computer monitor, CRT, digital screen, LED, LCD, X-ray, compressed digitized image such as JPEG, MPEG, etc. video image or a hand held device (i.e. a Palm Pilot™, calculator, etc). The display may be separated from the means for comparing, such that the display receives the quantitative probability of recurrence of prostatic cancer from the useful memory.

The apparatus may further comprise a database, which stores the correlation of factors and is accessible by the means for comparing. The apparatus also may comprise an input device that inputs the identical set of factors determined from the patient diagnosed as having prostatic cancer into the apparatus. Useful input devices include, but are not limited to a keypad, keyboard, stored data, touch screen, voice activated system, downloadable program or data, digital interface, hand-held device, or infra-red signal device. The input device may optionally store the identical set of factors in a means for storing that is accessible by the means for comparing. This means for storing may comprise include, but are not limited to, random access memory, read-only memory, disk, virtual memory, processors, and the like. Further, data may be stored in paper form on charts or graphs, or the like.

The apparatus may further comprise a transmission medium for transmitting the selected set of factors. This transmission medium may be coupled to the means for comparing and the correlation of factors. Additionally, or alternately, the apparatus may comprise a transmission medium for transmitting the identical set of factors determined from the patient diagnosed as having prostatic cancer. This transmission medium may be coupled to the means for comparing and the correlation of factors. For example, the transmission medium may include a global communication network, such as the Internet. Such a network may be accessed by means of personal computers or internet appliances, or the like.

The means for comparing may comprise a multi-purpose or dedicated processor. For example, the means for comparing may include an object oriented program having libraries, the libraries storing the correlation of factors. Alternately, apparatus according to the present invention may comprise storing means for storing the nomogram, means for inputting the identical set of factors determined from the patient into the apparatus, and display means for displaying the quantitive probability of recurrence of prostatic cancer. The storing means may comprise any suitable device, such as those described earlier, including, but not limited to, random access memory, read-only memory, one or more disks, virtual memory, processors, and the like. The means for inputting may comprise any suitable device, such as those described earlier, including, but not limited to, keypad, keyboard, stored data, touch screen, voice activated system, downloadable program or data, digital interface, hand-held device, or infra-red signal device. The display means may comprise any suitable device, such as those described earlier, including, but not limited to, a computer monitor, CRT, digital screen, LED, LCD, X-ray, compressed digitized image such as JPEG, MPEG, etc., video image, or hand held devices (i.e. Palm Pilot™, calculator, etc).

Still another embodiment of the invention is directed to an apparatus for predicting a quantitative probability of disease recurrence in a patient with prostatic cancer following a radical prostatectomy. The apparatus comprises a correlation of clinical and pathological factors determined for each of a plurality of persons previously diagnosed with prostatic cancer and having been treated by radical prostatectomy with incidence of recurrence of prostatic cancer for each person of the plurality of persons, wherein the selected set of factors comprises specimen Gleason sum, surgical margin status, presence of seminal vesicle invasion, and lymph node status, and a means for comparing an identical set of factors determined from the patient diagnosed as having prostatic cancer to the correlation to predict the quantitative probability of recurrence of prostatic cancer in the patient following radical prostatectomy.

Yet a further embodiment of the invention is directed to a nomogram for the graphic representation of a quantitative probability that a patient with prostate cancer will remain free of disease following radical prostatectomy. The nomogram comprises a plurality of scales and a solid support, the plurality of scales being disposed on the support and comprising a specimen Gleason sum scale, a surgical margin status scale, a presence of seminal vesicle invasion scale, a lymph node status scale, a points scale, a total points scale and a predictor scale, wherein the specimen Gleason sum scale, surgical margin status scale, presence of seminal vesicle invasion scale, and lymph node status scale each have values on the scales, and wherein the specimen Gleason sum scale, the surgical margin status scale, the presence of seminal vesicle invasion scale, and the lymph node status scale are disposed on the solid support with respect to the points scale so that each of the values on the specimen Gleason sum scale, the surgical margin status scale, the presence of seminal vesicle invasion scale, and the lymph node status scale can be correlated with values on the points scale, and wherein the total points scale has values on the total points scale and wherein the total points scale is disposed on the solid support with respect to the predictor scale so that the values on the total points scale may be correlated with values on the predictor scale, such that the values on the points scale correlating with the patient's specimen Gleason sum, surgical margin status, presence of seminal vesicle invasion, and lymph node status may be added together to yield a total points value, and the total points value may be correlated with the predictor scale to predict the quantitative probability of recurrence. This nomogram may be embodied in a computerized form, and incorporate the various elements as disclosed above. For example, the nomogram may be stored in a memory. The nomogram may comprise a display that displays the nomogram.

Another embodiment is directed to a method to predict a postoperative prognosis in a patient following radical prostatectomy, comprising the steps of determining a set of factors comprising the patient's specimen Gleason sum, surgical margin status, presence of seminal vesicle invasion, and lymph node status, matching the factors to the values on the specimen Gleason sum scale, the surgical margin status scale, the presence of seminal vesicle invasion scale and the lymph node status scale of the nomogram of the previous embodiment, determining a separate point value for each of the factors, adding the separate point values together to yield a total points value, and correlating the total points value with a value on the predictor scale of the nomogram to determine the prognosis of the patient.

Still a further embodiment is directed to a method for predicting a quantitative probability of recurrence of prostatic cancer in a patient following treatment with an identified therapy comprising the steps of correlating a selected set of factors determined for each of a plurality of persons previously diagnosed with prostatic cancer and having been treated by the identified therapy with incidence of recurrence of prostatic cancer for each person of the plurality of persons to generate a functional representation of the correlation, wherein the functional representation of the correlation comprises a separate factor evaluation system for each of the factors, and wherein each of the factor evaluation systems provides a value corresponding with a status of the corresponding factor, which value may be summed with values corresponding to the status of the other factors in the selected set to derive a quantitative probability of recurrence of prostatic cancer following the identified therapy, determining the status of an identical set of factors for the patient, applying the status of each of the patient's set of factors to the corresponding factor evaluation system to determine a patient value for each of the factors, and summing the patient's values to derive the quantitative probability of recurrence of prostatic cancer in the patient following the identified therapy. Preferably, the selected set of factors comprises at least two factors selected from the group consisting of pretreatment PSA level, combined Gleason grade, specimen Gleason sum, clinical stage, surgical margin status, prostatic capsular invasion level, extraprostatic extension, level of extraprostatic extension, apoptotic index, maximum cancer length in a core, total length of cancer in the biopsy cores, percent of cores positive, percent of cancer in one or more cores, percent of high grade cancer in one or more cores, total tumor volume, zone of location of the cancer, presence of seminal vesicle invasion, type of seminal vesicle invasion, p53, Ki-67, p27, DNA ploidy status, lymph node status, and lymphovascular invasion.

The factor evaluation systems preferably comprise a scale having values corresponding to status of each factor and the step of applying comprises matching the patient's status for each of the factors to its status on the corresponding scale to determine the patient's values for each of the factors. The functional representation may be a nomogram. The method may further comprise the step of displaying the functional representation on a display, such as the display devices previously described. The method may further comprise the step of inputting the identical set of factors for the patient with an input device.

The steps of correlating, determining, applying, and summing maybe executed by one or more processors or by one or more virtual computer programs. The correlating step may include accessing a memory storing the selected set of factors. The correlating step may include generating the functional representation and displaying the functional representation on a display. The displaying step may include transmitting the functional representation to the display. Alternately, the displaying step may include downloading the functional representation from a source. The source may comprise a an internet service provider, website, memory, database, internet, intranet, ethernet, or mainframe, or the like. The determining step may include accessing a memory storing the identical set of factors. The method may further comprise the step of storing any of the set of factors to a memory or to a database. The method may further comprise the step of transmitting the quantitative probability of recurrence of prostatic cancer. In this method, the identified therapy may be any desired therapy, including, but not limited to radical prostatectomy, radiation therapy, brachytherapy, hormonal therapy, cryotherapy, chemotherapy and combinations thereof.

Another embodiment is directed to a method for predicting a quantitative probability of recurrence of prostatic cancer following radical prostatectomy in a patient diagnosed as having prostatic cancer comprising the steps of: correlating a selected set of preoperative factors determined for each of a plurality of persons previously diagnosed with prostatic cancer and having been treated by radical prostatectomy with incidence of recurrence of prostatic cancer for each person of the plurality of persons to generate a functional representation of the correlation, wherein the selected set of preoperative factors comprises pretreatment PSA level, combined Gleason grade, clinical stage, and one or more supplemental factors selected from the group consisting of apoptotic index, maximum cancer length in a core, percent of cores positive, percent of cancer in one or more cores, percent of high grade cancer in one or more cores and total length of cancer in the biopsy cores, wherein the functional representation of the correlation comprises a pretreatment PSA level scale, a clinical stage scale, a combined Gleason grade scale, one or more supplemental factor scales for each of the one or more supplemental factors, a points scale, a total points scale, and a predictor scale, and wherein the pretreatment PSA level scale, the clinical stage scale, the combined Gleason grade scale and the one or more supplemental factors scales each have values on the scales which can be correlated with values on the points scale, and wherein the total points scale has values which may be correlated with values on the predictor scale; determining an identical set of preoperative factors for the patient; matching the patient's pretreatment PSA level to a corresponding value on the pretreatment PSA level scale, and determining a first point value from the corresponding value on the points scale; matching the patient's combined Gleason grade to a corresponding value on the combined Gleason grade scale, and determining a second point value from the corresponding value on the points scale; matching the patient's clinical stage to a corresponding value on the clinical stage scale, and determining a third point value from the corresponding value on the points scale; matching the patient's one or more supplemental factors to one or more corresponding values on the one or more supplemental factor scales to determine one or more supplemental point values on the points scale; adding the first, second and third and one or more supplemental point values together to get a patient total points value; matching the patient total points value to a corresponding value on the total points scale; and correlating the corresponding value on the total points scale with a value on the predictor scale to predict the quantitative probability of recurrence of prostatic cancer in the patient following radical prostatectomy.

The steps of this method may be executed on a computer processing device. The computer processing device preferably displays the values to a user. Alternately, the steps are executed on an embedded processor.

In still another embodiment, the invention is directed to a postoperative method for predicting a quantitative probability of recurrence of prostatic cancer in a patient who has previously undergone a radical prostatectomy comprising the steps of: correlating a selected set of factors determined for each of a plurality of persons previously diagnosed with prostatic cancer with incidence of recurrence of prostatic cancer for each person of the plurality to generate a functional representation of the correlation, wherein the selected set of factors comprises specimen Gleason sum, surgical margin status, presence of seminal vesicle invasion, and lymph node status, wherein the plurality of persons comprises men having undergone radical prostatectomy, wherein the functional representation of the correlation comprises a specimen Gleason sum scale, a surgical margin status scale, a presence of seminal vesicle invasion scale, a lymph node status scale, a points scale, a total points scale, and a predictor scale, and wherein the specimen Gleason sum scale, the surgical margin status scale, the presence of seminal vesicle invasion scale, and the lymph node status scale each have values on the scales which can be correlated with values on the points scale, and wherein the total points scale has values on the scale which may be correlated with values on the predictor scale; determining an identical set of factors for the patient; matching the patient's specimen Gleason sum to a corresponding value on the specimen Gleason sum scale, and determining a first point value from the corresponding value on the points scale; matching the patient's surgical margin status to a corresponding value on the surgical margin status scale, and determining a second point value from the corresponding value on the points scale; matching the patient's presence of seminal vesicle invasion to a corresponding value on the presence of seminal vesicle invasion scale, and determining a third point value from the corresponding value on the points scale; matching the patient's lymph node status to a corresponding value on the lymph node status scale, and determining a fourth point value from the corresponding value on the points scale; adding the first, second, third, and fourth point values together to get a patient total points value; matching the patient total points value to a corresponding value on the total points scale; and correlating the corresponding value on the total points scale with a value on the predictor scale to predict the quantitative probability of recurrence of prostatic cancer for the patient.

Optionally, the selected set of factors further comprises one or more supplemental factors selected from the group consisting of total tumor volume, pretreatment PSA, prostatic capsular invasion, zone of location of the cancer, p53, Ki-67, p27, level of extraprostatic extension, DNA ploidy status, type of seminal vesicle invasion, clinical stage and lymphovascular invasion and the functional representation further comprises one or more supplemental factor scales for each of the one or more supplemental factors, the one or more supplemental factor scales each having values on the scales which can be correlated with the values on the points scale, and wherein the method further comprises the steps of: determining the patient's one or more supplemental factors; matching the patient's one or more supplemental factors to one or more corresponding values on the one or more supplemental factor scales to determine one or more supplemental point values on the points scale; and adding the one or more supplemental point values to the first, second, third, and fourth point values to determine the patient total points value.

As with the previous embodiment, the steps may be executed on a computer processing device, such as one in which the computer processing device displays the values to a user. The steps may be executed on an embedded processor.

In a further embodiment, the intention is directed to a method of using a computer processor for predicting a quantitative probability of recurrence of prostatic cancer in a patient following treatment with an identified therapy comprising the steps of: correlating a selected set of factors determined for each of a plurality of persons previously diagnosed with prostatic cancer and having been treated by the identified therapy with incidence of recurrence of prostatic cancer for each person of the plurality of persons to generate a functional representation of the correlation using the computer processor, wherein the functional representation of the correlation comprises a separate factor evaluation system for each of the factors, and wherein each of the factor evaluation systems provides a value corresponding with a status of the corresponding factor, which value may be summed with values corresponding to the status of the other factors in the selected set to derive a quantitative probability of recurrence of prostatic cancer following the identified therapy; determining the status of an identical set of factors for the patient using the computer processor; applying the status of each of the patient's set of factors to the corresponding factor evaluation system to determine a patient value for each of the factors using the computer processor; and summing the patient's values to derive the quantitative probability of recurrence of prostatic cancer in the patient following the identified therapy. Preferably, the selected set of factors comprises at least two factors selected from the group consisting of pretreatment PSA level, combined Gleason grade, specimen Gleason sum, clinical stage, surgical margin status, prostatic capsular invasion level, extraprostatic extension, level of extraprostatic extension, apoptotic index, maximum cancer length in a core, total length of cancer in the biopsy cores, percent of cores positive, percent of cancer in one or more cores, percent of high grade cancer in one or more cores, total tumor volume, zone of location of the cancer, presence of seminal vesicle invasion, type of seminal vesicle invasion, p53, Ki-67, p27, DNA ploidy status, lymph node status, and lymphovascular invasion A memory may be coupled to or integral with the computer processor. An input device may be coupled to the computer processor. A display may be coupled to the computer processor which display receives data from the computer processor.

In still another embodiment is directed to a computerized method for predicting a quantitative probability of recurrence of prostatic cancer in a patient following treatment with an identified therapy comprising the steps of: correlating a selected set of factors determined for each of a plurality of persons previously diagnosed with prostatic cancer and having been treated by the identified therapy with incidence of recurrence of prostatic cancer for each person of the plurality of persons to generate a functional representation of the correlation, wherein the functional representation of the correlation comprises a separate factor evaluation system for each of the factors, and wherein each of the factor evaluation systems provides a value corresponding with a status of the corresponding factor, which value may be summed with values corresponding to the status of the other factors in the selected set to derive a quantitative probability of recurrence of prostatic cancer following the identified therapy; determining the status of an identical set of factors for the patient; applying the status of each of the patient's set of factors to the corresponding factor evaluation system to determine a patient value for each of the factors; and summing the patient's values to derive the quantitative probability of recurrence of prostatic cancer in the patient following the identified therapy. Preferably, the selected set of factors comprises at least two factors selected from the group consisting of pretreatment PSA level, combined Gleason grade, specimen Gleason sum, clinical stage, surgical margin status, prostatic capsular invasion level, extraprostatic extension, level of extraprostatic extension, apoptotic index, maximum cancer length in a core, total length of cancer in the biopsy cores, percent of cores positive, percent of cancer in one or more cores, percent of high grade cancer in one or more cores, total tumor volume, zone of location of the cancer, presence of seminal vesicle invasion, type of seminal vesicle invasion, p53, Ki-67, p27, DNA ploidy status, lymph node status, and lymphovascular invasion.

Other embodiments and advantages of the invention are set forth, in part, in the description which follows and, in part, will be obvious from this description and may be learned from the practice of the invention.

DESCRIPTION OF THE DRAWINGS

FIG. 7-1 Flow chart depicting software logic of the invention.

FIG. 7-2 Continuation of software logic from FIG. 7-1.

DESCRIPTION OF THE INVENTION

Figure 1:
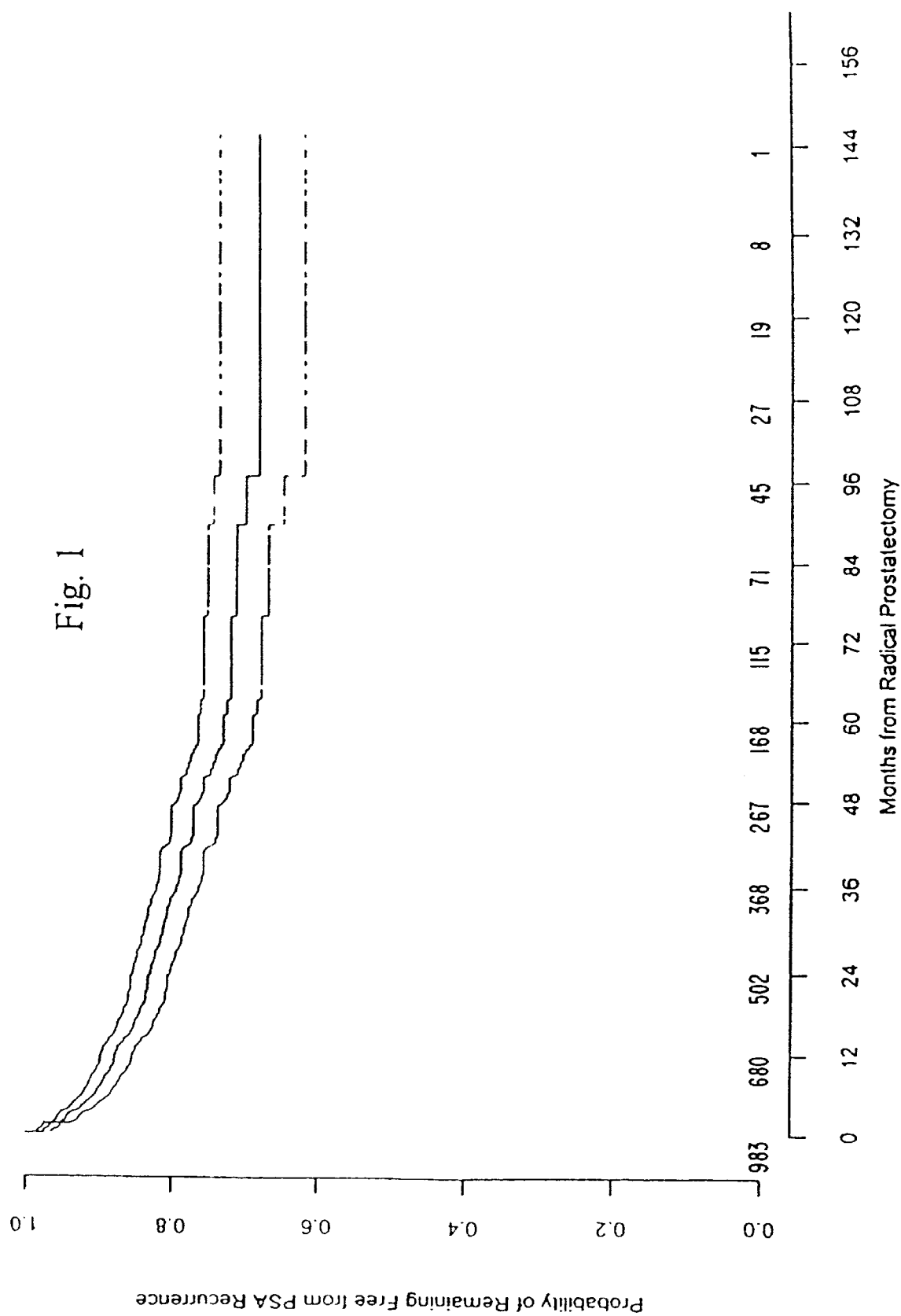
FIG. 1 Graph of overall recurrence-free probabilities following radical prostatectomy for the preoperative nomograms of FIGS. 2A and 2B.

As embodied and broadly described herein, the present invention is directed to methods and apparatus for predicting probability of disease recurrence following radical prostatectomy using routinely performed factors. The invention includes nomograms that can be used preoperatively and postoperatively to aid in selection of an appropriate course or courses of therapy.

a. Embodiments Using Preoperative Variables

The present invention provides for nomograms to predict disease recurrence using clinical factors available prior to surgery, to aid patients considering radical prostatectomy to treat clinically localized prostate cancer. The preoperative nomograms predict probability of disease recurrence after radical prostatectomy for localized prostate cancer (cT1–T3a N0 or NX M0 or MX) using routinely available preoperative factors, to assist the physician and patient in deciding whether or not radical prostatectomy is an acceptable treatment option. The present invention also provides for postoperative nomograms using selected variables. These nomograms can be used in clinical decision making by the clinician and patient and can be used to identify patients at high risk of disease recurrence who may benefit from neoadjuvant treatment protocols.

With respect to the preferred embodiments of the preoperative nomogram, using Cox proportional hazards regression, clinical data and disease follow-up were modeled for 983 men with clinical stage cT1–T3a N0 or NX M0 or MX prostate cancer who were treated with radical prostatectomy at The Methodist Hospital in Houston, Tex. Clinical data included pretreatment prostate specific antigen, biopsy Gleason scores, and clinical stage. Treatment failure was recorded when there was either clinical evidence of disease recurrence, arising serum prostate specific antigen level of 0.4 ng/mL or greater, or initiation of adjuvant therapy. Validation was performed on this set of men as well as a separate sample of 168 men, also from The Methodist Hospital. Both groups of men came from the SPORE Prostate Information System database.

The 983 men modeled were selected from a group of 1055 patients. Specifically, 1055 patients admitted between June 1983 and December 1996 to The Methodist Hospital with the intent to treat their clinically localized prostate cancer (cT1–T3a N0 or NX M0 or MX) with radical retropubic prostatectomy (RRP) were potential candidates for this analysis. One urologist treated all patients. Pelvic lymph node dissections were performed on all men, and RRP was aborted in 24 of 55 patients who were found to have positive nodes prior to RRP. These men were not excluded from analysis. Excluded from analysis were 55 men initially treated with definitive radiotherapy, and 1 treated with cryotherapy, who had a "salvage" radical prostatectomy for delayed local recurrence of cancer. (E. Rogers et al., J Urol 153:104–10, 1995). Sixteen men had no disease follow-up information and were also excluded. For comparison with other series, and not used as predictor or outcome variables, the final pathologic stage (M. Ohori et al., Cancer 74:104–14, 1994) distribution of the remaining 983 men was the following: pT1-2N0 (54.2%), pT3a, bN0 (27.1%), pT3cN0 (9.1%), and pT1-3N+(9.6%). Surgical margins were reported as positive in 15%. The mean age was 63 years (range 38–81), and 85% of the patients were Caucasian. The following routinely performed clinical variables were selected as predictors of recurrence: pretreatment serum PSA levels, primary and secondary Gleason grade in the biopsy specimen (D. F. Gleason, Urologic Pathology: The Prostate, 171–197, Tannebaum M., editor. Lea and Febiger 1997) and clinical stage (assigned using the TNM system) (M. Ohori et al., Cancer 74:104–14, 1994). The pretreatment PSA was the level measured by the Hybritech or comparable assay before biopsy when available.

Otherwise, the PSA level measured in the study laboratory the fewest number of days before radical prostatectomy was used. Some patients treated before PSA came into routine clinical practice in 1987 had a serum bank specimen available for retrospective analysis in this laboratory. Biopsy Gleason grade and clinical stage were assigned by a single pathologist and urologist respectively. In the interest of a parsimonious model, emerging markers with less demonstrated predictive value (e.g., free PSA) were not included in this analysis. Missing values for PSA (N=75), and biopsy Gleason grade (N=16) were imputed using the transcan function in S-Plus software. (F. E. Harrell, Transcan: an S-Plus function, 1995; F. E. Harrell et al., Stats. Med 15:361–387, 1996). This approach uses all of the predictor variables to calculate the value of the missing variable without reference to the outcome. Imputing a missing value was preferred to deleting a patient's entire medical record, so that the maximum information is utilized and the bias that may result from a deleted case was avoided. (F. E. Harrell, Transcan: an S-Plus function, 1995; F. E. Harrell et al., Stats. Med 15:361–387, 1996). However, for comparison, a data set consisting of only complete records was modeled as well. The descriptive statistics after imputing appear in Tables 1–3.

Tables 1–3

Clinical characteristics of 983 patients undergoing radical retropubic prostatectomy after missing values were imputed. "UICC stage" refers to the preoperative clinical stages promulgated by Union International Contre le Cancer. (F. H. Schröder et al., The Prostate Supplement 4:129–138, 1992; M. Ohori et al., Cancer 74:104–14, 1994). "N" refers to the number of patients in each category. "%" refers to the percent of all patients falling within the noted category.

TABLE 1

| UICC STAGE* | N (%) |
|---|---|
| T1a | 33 (3.3) |
| T1b | 50 (5.1) |
| T1c | 148 (15.1) |
| T2a | 266 (27.1) |
| T2b | 246 (25.0) |
| T2c | 182 (18.5) |
| T3a | 58 (5.9) |
| TOTAL | 983 (100) |

TABLE 2

| Gleason Grade in Biopsy** | | |
|---|---|---|
| Primary | Secondary | N (%) |
| 1–2 | 1–2 | 108 (11.0) |
| 1–2 | 3 | 158 (16.1) |
| 3 | 1–2 | 65 (6.6) |
| 3 | 3 | 340 (34.6) |
| 1–3 | 4–5 | 213 (21.7) |
| 4–5 | 1–5 | 99 (10.1) |

TABLE 3

| Pretreatment PSA*** | N (%) |
|---|---|
| 0.1–4.0 | 217 (22.1) |
| 4.1–10.0 | 472 (48.0) |

TABLE 3-continued

| Pretreatment PSA*** | N (%) |
|---|---|
| 10.1–20.0 | 187 (19.0) |
| 20.1–100.0 | 107 (10.9) |

Median 6.8, Mean 9.9 ng/mL

*UICC Stage T1: clinically inapparent tumor, not palpable nor visible by imaging; T1a: tumor an incidental histologic finding, 5% or more of tissue resected; T1b: tumor an incidental histologic finding, less than 5% of tissue resected; T1c: tumor identified by needle biopsy (e.g., because of elevated serum prostate-specific antigen). UICC Stage T2: tumor confined within the prostate; T2a: tumor involves half a lobe or less; T2b: tumor involves more than half a lobe but not both lobes; T2c: tumor involves both lobes; T3: tumor extends through the prostate capsule; T3a: unilateral extracapsular extension.

**Gleason grades 1–2 are well differentiated, 3 is moderately differentiated, 4–5 are poorly differentiated.

***Median serum prostate—specific antigen (PSA) level for all patients 6.8 ng/mL (range, 0.1–100.0 ng/mL); mean serum PSA level for all patients, 9.9 ng/mL (95% confidence interval=9.24–10.54 ng/mL).

Treatment failure was defined as either clinical evidence of cancer recurrence (observed in only 2 PSA-era patients before the PSA became detectable) or a postoperative PSA≧0.4 ng/mL followed by a second PSA higher than the first. Patients who were treated with hormonal therapy (N=8) or radiotherapy (N=25) after surgery but before documented recurrence were treated as failures at the time of second therapy. Patients who had their RRP aborted due to positive nodes (N=24) were considered immediate treatment failures.

Figure 2A:
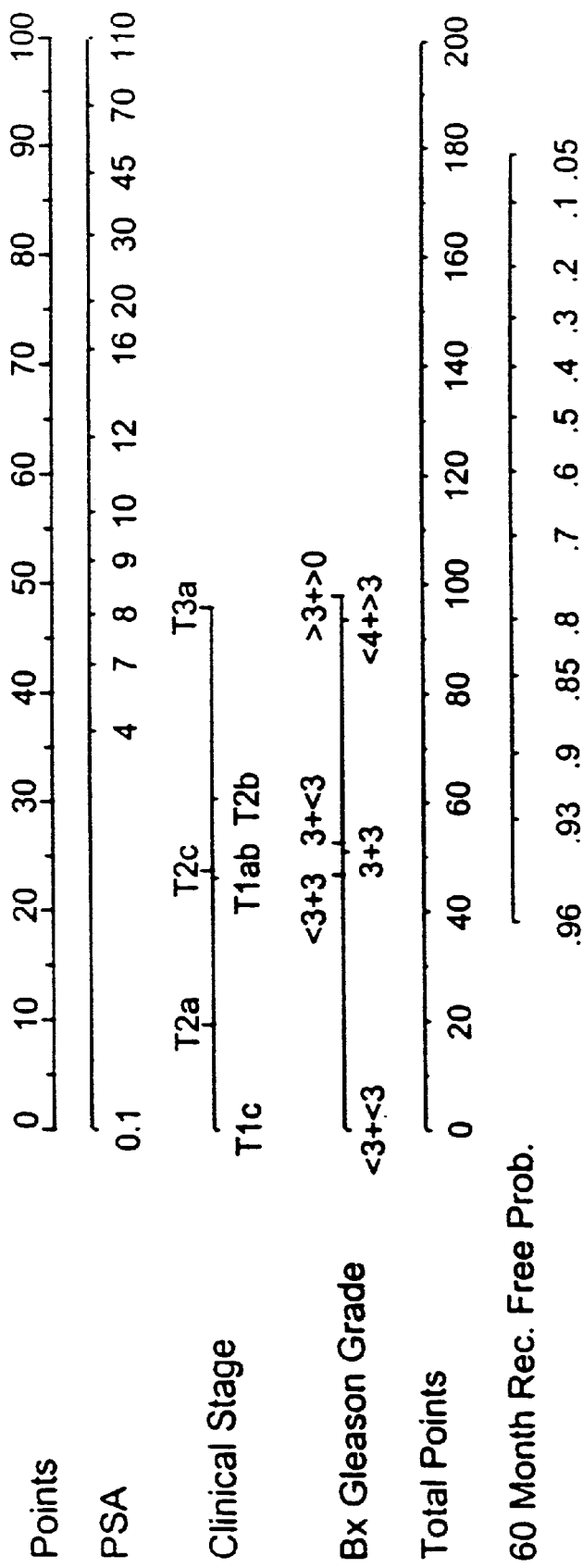
FIG. 2A A first nomogram useful for the preoperative assessment of probability of cancer recurrence following radical prostatectomy.
Figure 2B:
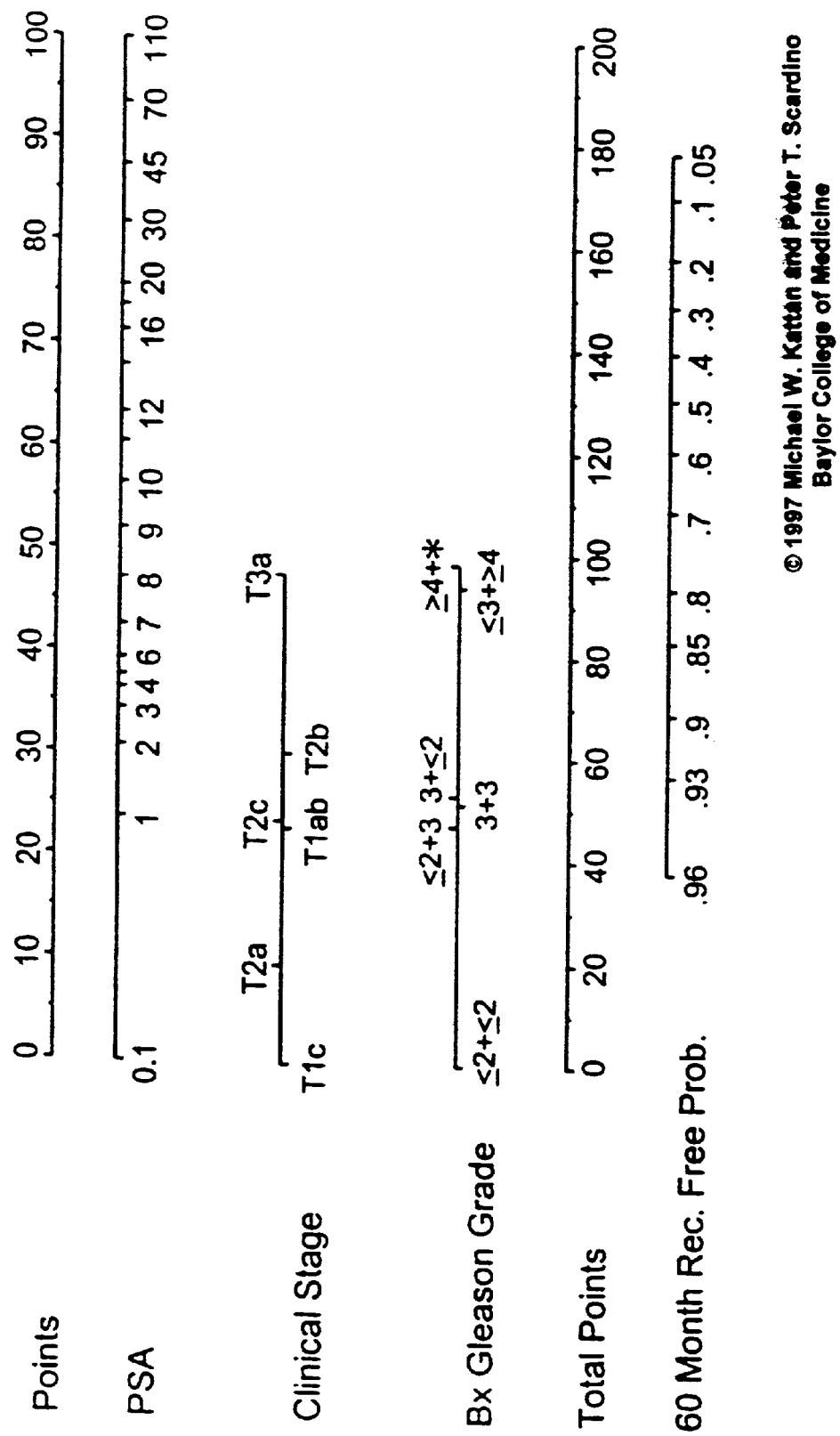
FIG. 2B A second nomogram useful for the preoperative assessment of probability of cancer recurrence following radical prostatectomy.

Estimates of the probability of remaining free from recurrence were calculated using the Kaplan-Meier method. Multivariable analysis was conducted using Cox proportional hazards regression. PSA had a skewed distribution and suspected nonlinear effect, so it was modeled as a restricted cubic spline (F. E. Harrell et al., Stats Med 15:361–387, 1996) of its log. Primary and secondary biopsy Gleason grades, each from 1 to 5, were collapsed into low (1–2), moderate (3), and high (4–5) grade categories due to small frequencies at the extremes. A potential interactive effect was anticipated due to the nature of the Gleason scoring system, so the Gleason primary and secondary grades were combined into 6 categories to come up with six combined Gleason grades in the biopsy specimen ("Bx Gleason Grade") In one embodiment of the nomogram the six categories used were: <3+<3, <3+3, 3+<3, 3+3, <4+>3 and >3+>0, based on frequency counts (FIG. 2A). In another embodiment of the nomogram, the six categories were: ≦2+≦2, ≦2+3, 3+≦2, 3+3, ≦3+≧4, and ≧4+any, also based on frequency counts. (FIG. 2B). Similarly, clinical stages T1a (n=33) and T1b (n=50) were combined because of the small numbers of each and the similar method of detection of cancer. Decisions with respect to the coding of the nomogram variables were made prior to modeling. The Cox model was the basis for a nomogram.

Validation of the nomograms of FIGS. 2A and 2B contained three components. First, the nomograms were subjected to bootstrapping, with 200 re-samples, as a means of calculating a relatively unbiased measure of its ability to discriminate among patients, as quantified by the area under the receiver operating characteristic (ROC) curve (J. A. Hanley et al., Radiology 143:29–36, 1982). With censored data, the ROC calculation (F. E. Harrell et al., Stats Med 15:361–387, 1996) is slightly modified from its normal method. Nonetheless, its interpretation is similar. The area under the ROC curve is the probability that, given two randomly drawn patients, the patient who recurs first had a higher probability of recurrence. Note that this calculation assumes that the patient with the shorter follow-up recurred. If both patients recur at the same time, or the non-recurrent patient has shorter follow-up, the probability does not apply to that pair of patients. The second validation component was to compare predicted probability of recurrence vs. actual recurrence (i.e., nomogram calibration) on the 983 patients, again using 200 bootstrap re-samples to reduce overfit bias which would overstate the accuracy of the nomogram. Finally, the third validation component was simply to apply the nomograms to the 168 patients not included in the modeling sample. These 168 patients were treated by 5 surgeons at Baylor College of Medicine. These were the patients with complete records only, and no values were imputed. As with the modeling sample, pretreatment PSA was measured with the Hybritech assay immediately before biopsy (if available) or before radical prostatectomy, and Gleason grading was done by a single pathologist. Each individual surgeon assigned the clinical staging in his/her patients. Patients were accrued between October 1990 and December 1996. For these patients, their predicted probability of 5 year recurrence was compared with actual follow-up, and the area under the ROC curve for these men was calculated. Statistical analyses were performed using S-Plus software (PC Version 3.3, Redmond Wash.) with the Design functions (F. E. Harrell, Programs available from statlib@lib.stat.cmu.edu, 1994).

Of the 983 patients analyzed, 196 had evidence of recurrence of prostate cancer following radical prostatectomy. For patients without disease recurrence, median and maximum follow-up were 30 and 146 months, respectively, and 168 patients had at least 60 months disease-free follow-up. Overall Kaplan-Meier recurrence-free probabilities and their 95% confidence intervals appear in FIG. 1. The x-axis depicts months from radical prostatectomy and the y-axis depicts probability of remaining free from PSA recurrence. Numbers above the months indicate patients at risk of recurrence. The cohort 5-year recurrence-free probability was 73% (95% CI: 69% to 76%). Consistent with previous analysis of the hazard rates (O. Dillioglugil et al., Urology 50:93–99, 1997), recurrence beyond the 5-year point is rare (average annual hazard rate=0.014/year). No recurrences were observed later than 100 months, but the tail of the curve is retained in FIG. 1 to illustrate follow-up. PSA, biopsy combined Gleason grade, and clinical stage were all associated with recurrence (p<0.001) for each, suggesting that the model with all three variables is likely superior to a smaller model (e.g., with PSA alone). Strong evidence for violation of the proportional hazards assumption was not seen in analyses and plots of the Schoenfeld residuals.

Two preoperative nomograms were constructed based on the Cox model and appear in FIGS. 2A and 2B. The nomograms are each used by first locating a patient's position on each predictor variable scale (PSA through clinical stage). Each scale position has corresponding prognostic points (top axis). For example, a PSA of 4 contributes approximately 37 points; this is determined by comparing the location of the 4 value on the PSA axis to the Points scale above and drawing a vertical line between the 2 axes. The point values for all clinical predictor variables can be determined in a similar manner and can be summed to arrive at a Total Points value. This value is plotted on the Total Points axis (second from the bottom). A vertical line drawn from the Total Points axis straight down to the 60-month recurrence free probability axis will indicate the patient's probability of remaining free from cancer recurrence for 5 years assuming he remains alive and does not die of another cause first.

The area under the ROC curve was computed for the nomograms. Without bootstrapping, the area was 0.76. Because this is the value on the same data used in modeling, it likely overstates expected performance on future data. After bootstrapping, the area was estimated to be 0.74. The probability of 5-year recurrence was predicted for the separate sample of 168 patients. Of these men, 12 had disease recurrence. Nomogram predictions were compared with actual outcome, and the area under the ROC curve was calculated and found to be 0.79.

Figure 3:
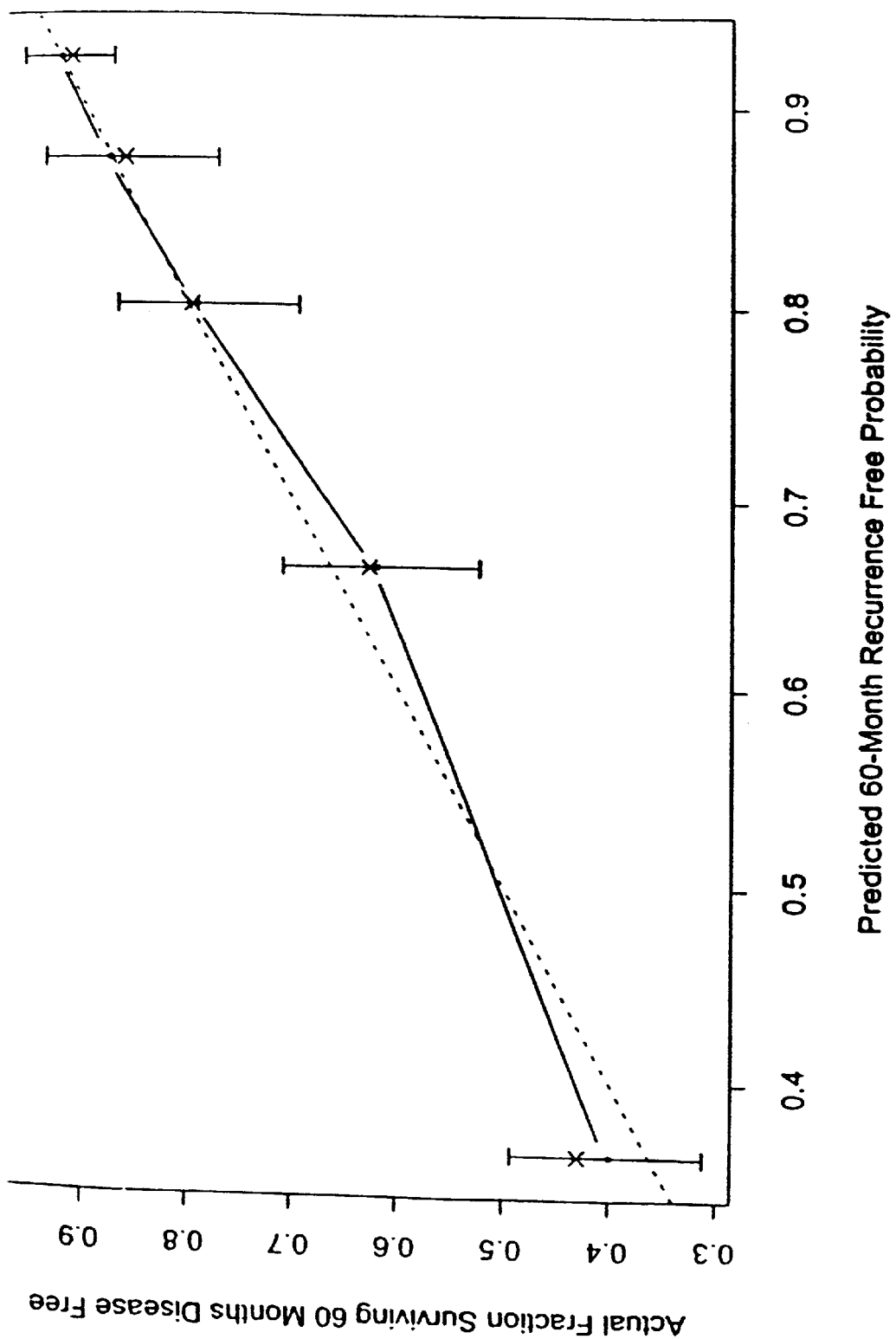
FIG. 3 Comparison of model predictions of FIGS. 2A and 2B with actual outcome.

FIG. 3 illustrates how the model predictions compare with actual outcome of the 983 patients. The x-axis is the nomogram prediction (predicted 60-month recurrence free probability) and the y-axis is the actual freedom from cancer recurrence of the 983 patients (actual fraction surviving 60 months disease free). The dotted line represents the performance of an ideal nomogram, in which predicted outcome perfectly corresponds with actual outcome. The performance of the nomograms of the present invention is plotted as the solid line that connects the dots, corresponding to sub-cohorts (based on predicted risk) within the dataset. The nomograms' predictions approximate the actual outcomes, since the dots are relatively close to the dotted line. The X's indicate bootstrap-corrected estimates of the predicted freedom from disease recurrence, which are more appropriate estimates of actual freedom from recurrence. Most of the X's are close to the dots, indicating that the nomograms' predictions using the modeled data (the dots) are near that expected with the new data (the X's), though there is some regression to the mean at the extremes. The vertical bars in FIG. 3 indicate 95% confidence intervals based on the bootstrap analysis. In general, the nomograms performances appear to be within 10% of actual outcome, and possibly slightly more accurate at very high levels of predicted probability. There are wider confidence intervals at lower predicted probabilities of recurrence.

Accordingly, one embodiment of the invention is directed to a method for predicting the probability of recurrence of prostatic cancer following radical prostatectomy in a patient diagnosed as having prostatic cancer. This method comprises correlating a selected set of preoperative clinical factors determined for each of a plurality of persons previously diagnosed with prostatic cancer and having been treated by radical prostatectomy with the incidence of recurrence of prostatic cancer for each person of said plurality of persons to generate a functional representation of the correlation, wherein said selected set of preoperative clinical factors comprises pretreatment serum PSA level, combined Gleason grade in the biopsy specimen and clinical stage; and matching an identical set of preoperative clinical factors determined from the patient diagnosed as having prostatic cancer to the functional representation to predict the probability of recurrence of prostatic cancer in the patient following radical prostatectomy. In an alternative embodiment, Gleason sum may be used instead of combined Gleason grade. The terms "correlation," "correlate" and "correlating" as used in connection with the present invention refer to a statistical association between factors and outcome, and may or may not be equivalent to a calculation of a statistical correlation coefficient such as a Pearson correlation coefficient or others.

In a preferred embodiment, the functional representation is a nomogram and the patient is a pre-surgical candidate or someone who has not yet been treated, although the method may also be used in a postoperative situation. In this preferred embodiment, the probability of recurrence of prostatic cancer is a probability of remaining free of prostatic cancer five years following radical prostatectomy. Disease recurrence may be characterized as an increased serum PSA level, preferably greater than or equal to 0.4 ng/mL. Alternatively, disease recurrence may be characterized by positive biopsy, bone scan, or other imaging test or clinical parameter. Recurrence may alternatively be defined as the need for or the application of further treatment for the cancer because of the high probability of subsequent recurrence of the cancer.

In a preferred embodiment, the plurality of persons comprises persons with clinically localized prostate cancer not treated previously by radiotherapy or cryotherapy, who have subsequently undergone radical prostatectomy. This group preferably comprises men diagnosed with prostate cancer between June 1983 and December 1996. In one preferred embodiment, the group comprises men admitted to The Methodist Hospital between June 1983 and December 1996. As will be clear to those of skill in the art, other suitable populations may also be used.

In a preferred embodiment, the nomogram is generated with a Cox proportional hazards regression model. (D. R. Cox, Regression models and life tables (with discussion), Journal of the Royal Statistical Society B34: 187–220, 1972). This method predicts survival-type outcomes using multiple predictor variables. The Cox proportional hazards regression method estimates the probability of reaching a certain end point, such as disease recurrence, over time.

In another embodiment, the nomogram may be generated with a neural network model (D. E. Rumelhart et al. (eds), Parallel Distributed Processing: Exploration in the Microstructure of Cognition Volume 1. Foundations. Cambridge, Mass, The MIT Press, 1986). This is a non-linear, feed-forward system of layered neurons which backpropagate prediction errors.

In another embodiment, the nomogram may be generated with a recursive partitioning model. (L. Breiman et al., Classification and Regression Trees. Monterey, Calif., Wadsworth and Brooks/Cole, 1984). Other models known to those skilled in the art may be alternatively be used.

Another embodiment of this invention is a nomogram for determining a preoperative probability of prostatic cancer recurrence as depicted or represented in FIGS. 2A or 2B. This nomogram may comprise an apparatus for predicting probability of disease recurrence in a patient with prostatic cancer following a radical prostatectomy, wherein the apparatus comprises a correlation of preoperative clinical factors determined for each of a plurality of persons previously diagnosed with prostatic cancer and having been treated by radical prostatectomy with incidence of recurrence of prostatic cancer for each person of said plurality of persons, wherein said selected set of preoperative clinical factors comprises pretreatment PSA level, combined Gleason grade in the biopsy specimen and clinical stage; and a means for matching an identical set of preoperative clinical factors determined from the patient diagnosed as having prostatic cancer to the correlation to predict the probability of recurrence of prostatic cancer in the patient following radical prostatectomy.

The combined grade in the biopsy specimen (Bx Gleason Grade) is defined as the Gleason grade of the most predominant pattern of prostate cancer present in the biopsy specimen (the primary Gleason grade) plus the second most predominant pattern (secondary Gleason grade), if that pattern comprises at least 5% of the estimated area of the cancer or the histologic sections of the biopsy specimen. For example, a man with a primary Gleason grade of 2 and a secondary Gleason grade of 3 is used in a preferred embodiment of the nomogram as a 2+3, not a 5, which obscures the individual components. Some authors have added the primary and secondary Gleason grades to determine a Gleason "sum," but the preferred embodiments of the preoperative nomograms of the invention illustrated in FIGS. 2A and 2B utilize the primary and secondary Gleason grade designated separately. Nonetheless, in an alternative embodiment of the invention, primary and secondary Gleason grades may be added together and the biopsy Gleason sum used. Note that in the preferred postoperative the embodiment depicted in FIG. 5, specimen Gleason sum is preferably used.

Another embodiment of the invention is directed to a preoperative nomogram which incorporates the three clinical factors of FIGS. 2A or 2B, as well as one or more of the following additional factors: 1) total length of cancer in the biopsy cores; 2) maximum cancer length in a core (Y. Goto et al., J. Urol. 156 (3): 1059–63, 1996); and (3) apoptotic index. Still another embodiment may comprise one or more of the foregoing factors with other routinely determined clinical factors. For example, and not by way of limitation, if available preoperatively, one or more of the factors p53, Ki-67 or p27 may be included. (A. M. F. Stapleton, et al., Cancer 82 (1):168–75, 1998; R. M. Yang et al., J Urol 159 (3):941–5, 1998).

With respect to the total length of cancer in the biopsy cores, it is customary during biopsy of the prostate to take multiple cores systematically representing each region of the prostate. For example, six stratified random cores may be taken from the apex, mid, and base portions of the right and left sides of the prostate. In a preferred embodiment, the total number of millimeters of cancer from the six cores is used. Alternatively, where either more or less than six cores are taken, the percentage of cancerous tissue may be used, calculated as the total number of millimeters of cancer in the cores divided by the total number of millimeters of tissue collected.

With respect to apoptotic index, this may be calculated from the histologic slides of the biopsy specimens as the number of apoptotic bodies divided by the total number of cancer cells counted. (A. M. F. Stapleton et al., Cancer 82 (1): 168–175, 1998).

The present invention further comprises a method to predict a preoperative prognosis in a patient comprising matching a patient-specific set of preoperative clinical factors comprising pretreatment PSA level, clinical stage, and combined Gleason grade in the biopsy to the nomogram of FIGS. 2A or 2B and determining the preoperative prognosis of the patient.

The nomogram or functional representation may assume any form, such as a computer program, world-wide-web page, or card, such as a laminated card. Any other suitable representation, picture, depiction or exemplification may be used. In one embodiment, the nomogram comprises a graphic representation of a probability that a patient with prostate cancer will remain free of disease following radical prostatectomy comprising a substrate or solid support, and a set of indicia on the substrate or solid support, the indicia comprising a pretreatment PSA level line, a clinical stage line, a combined Gleason grade in the biopsy line, a points line, a total points line and a predictor line, wherein said pretreatment PSA level line, clinical stage line and combined Gleason grade line each have values on a scale which can be correlated with values on a scale on the points line, and wherein said total points line has values on a scale which may be correlated with values on a scale on the predictor line, such that the value of each of the points correlating with the patient's pretreatment PSA level, combined Gleason grade, and clinical stage can be added together to yield a total points value, and the total points value is correlated with the predictor line to predict the probability of recurrence. The solid support is preferably a laminated card that can be easily carried on a person.

Following radical prostatectomy designed to cure the patient of his cancer, the serum PSA should become undetectable. (A. Stein et al., J. Urol. 147:942, 1992). Measurable levels of PSA after surgery provide evidence of disease recurrence which may precede detection of local or distant recurrence by many months to years. (A. W. Partin et al., Urol. Clin. North Am. 20(4):713–725, 1994). Although clinical experience with elevated serum PSA levels after radical prostatectomy is not yet mature enough to quantify an association with cancer specific mortality, elevated PSA levels are a reasonable measure of the ability of radical prostatectomy to cure a patient with prostate cancer, provided that the follow-up is long enough. This association has been demonstrated for patients with a rising PSA after non-hormonal systemic therapy for advanced prostate cancer, for example, in which men with recurrent cancer evidenced by a rising PSA are more likely to die of prostate cancer earlier than men whose PSA does not rise (R. Sridhara et al., J. Clin. Oncol. 13:2944–2953, 1995). Serum PSA after radical prostatectomy has been used as an endpoint for treatment efficacy to develop a model which predicts treatment failure. The recurrence decision rule of two PSAs equal to or above 0.4 ng/mL and rising was used as it is relatively safe from indicating false positives, which are particularly undesirable for the patient. It is true that the cutoff choice would affect the nomograms' predicted probabilities, so the results of the nomograms may be somewhat different than the actual outcome of patients at centers which use a different PSA cutoff rule. Furthermore, using a particular level of PSA as an event indicates that PSA follow-up data are interval-censored (occurring between two time points) (F.J. Dorey et al., Stats. in Med. 12:1589–1603, 1993) rather than right-censored (simply unknown after last follow-up), as modeled. However, adjuvant treatment decisions are often based on observed PSA recurrences, so that this endpoint is more useful clinically than the true PSA recurrence time.

The interest in PSA recurrence as an endpoint of a preoperative model motivated the survival-type analysis used in the preoperative nomograms of the present invention. In addition to serving as a prognostic tool, the nomograms in FIGS. 2A or 2B are useful for interpreting the underlying Cox model. PSA is influential across its spectrum, though patients with a very high PSA are rarely considered good candidates for surgery. The nomograms assign many points for cT3a and high grade disease, which is consistent with the clinical expectations of most physicians. The Cox model coefficients, and therefore the resulting nomograms, look very similar when only the complete records (without imputing) are modeled.

The preoperative nomograms of the present invention were based on patients who received radical prostatectomy, so they are most applicable to patients who otherwise appear to be candidates for surgery, rather than all patients diagnosed with prostate cancer. Given the selection by both patient and urologist (e.g., biopsy or serum criteria), either nomogram can be applied as a last step in the decision making process after the patient has decided upon radical retropubic prostatectomy as his treatment choice. The nomograms are not necessarily applicable for changing the mind of the patient who has decided against radical retropubic prostatectomy since his recurrence probability is not known; rather, they are designed to be used for revisiting the choice of surgery.

One way to apply either nomogram is to say, "Mr. X, if we had 100 men exactly like you, we would expect between <lower confidence limit> and <upper confidence limit> would remain free of their disease following radical prostatectomy for 5 years, assuming they did not die of something else first, and recurrence after 5 years is rare."

The nomograms are useful although they may not always predict with perfect accuracy. For example, with regard to the nomograms of FIGS. 2A and 2B, the area under the ROC curve on the validation sample was 0.79, while the bootstrap corrected estimate on the original sample was 0.74, which may be overly conservative in this case. Although the difference between the two may not be statistically significant, it is somewhat odd for the validation sample performance to be higher than even the uncorrected training sample performance (0.76), so true discriminatory power may be closer to 0.74 than 0.79 since the validation sample was small with few recurrences. Also, with respect to accuracy, the confidence intervals at the various predicted probabilities of recurrence (FIG. 3) are somewhat wide, at some levels as much as ±10%. At the individual patient level, this level of error is difficult to interpret since a single patient will either recur or not.

The cohort of patients in the original sample were all treated by a single surgeon and all data came from a single institution, which may affect generalizability to other urologists and institutions. Most of the patients were Caucasian, and while race has not been an independent predictor of recurrence in the data, others have found a postoperative racial effect, which may limit applicability for non-Caucasians (J. W. Moul et al., J. Urol. 155:1667–1673, 1996). Validation was performed on the data from different surgeons and accrued more recently than modeled in the nomogram. Application of the nomogram assumes that the effectiveness of the intervention (RRP) is similar at other institutions or in the community.

In addition to assisting the patient and physician in selecting an appropriate course of therapy, the nomograms of the present invention should also prove useful in clinical trials to identify patients appropriate for a trial, to quantify the expected benefit relative to baseline risk, to verify the effectiveness of randomization, to reduce the sample size requirements, and to facilitate comparisons across studies.

b. Embodiments Including Postoperative Variables

In addition to the various embodiments of the preoperative nomograms and method of using the nomograms discussed above, the present invention is also directed toward postoperative nomograms and methods of utilizing these nomograms to predict probability of disease recurrence following radical prostatectomy. This prognosis may be utilized, among other reasons, to determine the usefulness of adjuvant therapy in a patient following radical prostatectomy.

Accordingly, further embodiments of the present invention include a nomogram which incorporates clinical and pathologic factors, including postoperative factors, to predict probability of cancer recurrence after radical prostatectomy for clinically localized prostatic cancer. This nomogram predicts probability of disease recurrence using clinical and pathologic factors for patients who have received radical prostatectomy to treat clinically localized prostate cancer.

Using a Cox proportional hazards regression model, preoperative PSA and pathologic parameters were used to predict PSA or clinical recurrence in 996 men with clinical stage T1a–T3c N0-1M0 prostate cancer who were treated by radical prostatectomy by a single surgeon at The Methodist Hospital in Houston, Tex. Predictive factors included preoperative PSA level, specimen Gleason sum, prostatic capsular invasion level, surgical margin status, presence of seminal vesicle invasion, and lymph node status. Treatment failure was recorded when there was either clinical evidence of disease recurrence, a rising serum prostate specific antigen level (two measurements of 0.4 ng/mL or greater), or initiation of adjuvant therapy.

The 996 men modeled were selected from a group of 1145 patients. Specifically, 1145 patients who were treated with radical retropubic prostatectomy by a single surgeon during the period from June 1983 through June 1997 at The Methodist Hospital were potential candidates for this analysis. Pelvic lymph node dissections were performed on all men. Radical prostatectomy was aborted in 32 of the 58 patients who were found to have nodal metastases on frozen section analysis during the operation; these 32 men were excluded from the analysis. Also excluded were men treated with definitive radiotherapy (N=56), hormonal therapy (N=43), cryotherapy (N=3), or other radiotherapy (N=3) prior to the radical procedure. No disease follow-up information was available for 12 men, and they were also excluded. This left 996 men for analysis. Clinical stages were as follows: T1a (3.2%), T1b (4.3%), T1c (16.5%), T2a (27.1%), T2b (24.1%), T2c (18.5%), T3a (5.4%), T3b (0.1%), and T3c (0.89%). The final pathologic stage, determined by the study pathologist after the surgical specimen was sectioned serially at 5 mm intervals (M. Ohori et al., Cancer 74:104–114, 1994) was distributed as follows: pT2N0, confined to the prostate (55.8%); pT3aN0, extraprostatic extension, either focal or established (27.2%); pT3bN0, seminal vesicle involvement (9.1%); and pT2-3N1, pelvic lymph node metastasis (7.1%). Surgical margins were positive (ink touching cancer cells at the edge of the specimen) in 143 (14%) of the patients (M. Ohori et al., J. Urol. 154:1818–1824, 1995).

The level of prostate capsular invasion (PCI) with respect to the stroma of the prostate, prostatic capsule, and periprostatic soft tissue was classified as follows (T. M. Wheeler, Urol. Clin. North Am. 16:523, 1989; Shenkenberg, Rice L. et al., Cancer 49:1924, 1982):

Confined

Level 0 (L0) Tumor confined to prostatic stroma within the boundary of normal prostatic acini.

Level 1 (L1) Tumor confined to prostatic stroma, but outside the boundary of normal prostatic acini.

Level 2 (L2) Tumor confined to the prostate but within a layer more fibrous than muscular (capsule). Anteriorly and at the apex where "capsule" does not exist, the distinction between L1 and L2 is somewhat arbitrary.

Non-Confined

Level 3 (L3) Tumor invasive into the periprostatic adipose tissue or smooth muscle of bladder neck.

Level 3 focal (L3F) Tumor outside the prostate to a depth of less than one high-power field on no more than two separate sections.

Level 3 established (L3E) Any amount of extraprostatic tumor more than L3F.

Seminal vesicle involvement or invasion was defined as cancer within the muscular coat of the seminal vesicle, not simply tumor in the fat adjacent to the seminal vesicle (M. Ohori et al., Am. J. Surg. Pathol. 17(12): 1252–1261, 1993).

The median age of all patients was 63 years (range, 38–81 years), and 88% of the patients were Caucasian. For predictors of recurrence, selected preoperative serum PSA was selected in addition to the following routinely performed pathologic variables: Gleason sum in the surgical specimen (Gleason sum), prostatic capsular invasion level, surgical margin status, seminal vesicle invasion, and lymph node status. Biopsy Gleason grade and clinical stage were not included as predictor variables since they are both preoperative estimates of their pathologic counter parts, which were included as predictors. Preoperative PSA was measured by the Hybritech Tandem-R assay (Hybritech, Inc., San Diego, Calif.). In 64 patients (6.4%) treated before the PSA assay became available at the subject institution, no preoperative PSA level was determined. All prostates were totally embedded and sectioned by the whole-mount technique. A single pathologist measured the pathologic variables. In the interest of a parsimonious model, recently developed markers with less demonstrated predictive value (e.g., percent free PSA) were not included in the analysis. Missing values for PSA (N=64), prostatic capsular invasion (N=9), Gleason sum (N=4), surgical margins (N=4), seminal vesicle invasion (N=3), and lymph node status (N=3) were imputed with regression models (F. E. Harrell. Transcan: An S-Plus function. Program available from statlib@lib.stat.cmu.edu. Send e-mail 'send transcan from S,' 1995) containing all of the predictor variables to estimate the value of the missing predictor variable without reference to the outcome (PSA recurrence). Imputing a missing value is generally preferred to deleting a patient's entire medical record, so that the maximum information is utilized and the bias that may result from a deleted case can be avoided (F. E. Harrell et al., Stats. Med. 15:361–387, 1996). However, for comparison, a dataset consisting of only complete records was modeled as well. The descriptive statistics of all predictor variables after imputing appear in Table 4.

Table 4

Descriptive statistics of the predictor variables for 996 patients undergoing radical retropubic prostatectomy after missing values were imputed. "N" refers to the number of patients in each category. "%" refers to the percent of all patients falling within the noted category.

TABLE 4

|  | N | % |
|---|---|---|
| Gleason Sum | | |
| 3 | 2 | 0.2 |
| 4 | 5 | 0.5 |
| 5 | 106 | 10.6 |
| 6 | 350 | 35.1 |
| 7 | 454 | 45.6 |
| 8 | 61 | 6.1 |
| 9 | 14 | 1.4 |
| 10 | 4 | 0.4 |
| Prostatic Capsular Invasion | | |
| None | 184 | 18.5 |
| Invading Capsule | 396 | 39.8 |
| Focal | 152 | 15.3 |
| Established | 264 | 26.5 |

TABLE 4-continued

|  | N | % |
|---|---|---|
| Surgical Margins | | |
| Neg | 853 | 86.5 |
| Pos | 143 | 13.5 |
| Seminal Vesicle Invasion | | |
| No | 862 | 86.5 |
| Yes | 134 | 13.5 |
| Lymph Nodes | | |
| Neg | 925 | 92.9 |
| Pos | 71 | 7.1 |
| Preoperative PSA (ng/ml) | | |
| Min | 0.1 | |
| Median | 7.1 | |
| Mean | 10.4 | |
| Max | 100.0 | |

The time of treatment failure was defined as either the earliest date that the postoperative serum PSA level rose to 0.4 ng/mL or higher (N=124, confirmed by a second PSA higher than the first by any amount), or the earliest date of clinical evidence of cancer recurrence in patients with an undetectable PSA (N=4) or no PSA result (N=27) who developed recurrence before PSA was routinely measured. Patients who were treated with hormonal therapy (N=6) or radiotherapy (N=26) after surgery but before documented recurrence were treated as failures at the time of second therapy, due to interest in predicting who would eventually need second treatment for their cancer and the fact that adjuvant therapy may mask the appearance of measurable PSA in the serum. An additional two men, one of whom was treated before PSA was available as a clinical test, were reported as dead of prostate cancer with no available documentation to support evidence of recurrence prior to death, and these patients were considered treatment failures.

A separate sample for validation was composed of 322 patients with prostate cancer who had been treated by any one of five other surgeons at The Methodist Hospital. These were the patients with complete records only, and no values were imputed. As with the modeling sample, preoperative PSA was measured with the Hybritech assay immediately before biopsy (if available) or before radical prostatectomy, and pathologic variables were measured by a single pathologist. Each individual surgeon assigned the clinical staging for his/her patients. Patients were accrued from October 1990 through June 1997. All patients from both samples came from the Specialized Program of Research Excellence (SPORE) Prostate Information System database (Baylor College of Medicine).

Estimates of the probability of remaining free from recurrence were calculated with the Kaplan-Meier method. Multivariable analysis was conducted with Cox proportional hazards regression. The proportional hazards assumption was verified by tests of correlations with time and examination of residual plots. PSA had a skewed distribution and suspected nonlinear effect, so it was modeled as a restricted cubic spline (F. E. Harrell et al., Stats. Med. 15:361–387, 1996) of its log. Similarly, Gleason sum was suspected to be nonlinear and also modeled with a restricted cubic spline function. Prostate cancer within the confines of the glandular prostate or in the prostatic stroma but beyond the limit of the normal acini had to be combined as "None" due to no patients in first group experiencing recurrence, which would prohibit convergence of the Cox algorithm. All decisions with respect to the coding of the nomogram variables were made prior to modeling. This Cox model was the basis for a nomogram.

Validation of the postoperative nomogram contained three components. First, the nomogram was subjected to bootstrapping, with 200 re-samples, as a means of calculating a relatively unbiased measure of its ability to discriminate among patients, as quantified by the area under the receiver operating characteristic curve (J. A. Hanley et al., Radiology 143:29–36, 1982). With censored data, the receiver operating characteristic calculation (F. E. Harrell et al., Stats. Med. 15:361–387, 1996) was slightly modified from its normal method. Nonetheless, its interpretation was similar. The area under the receiver operating characteristic curve was the probability that, given two randomly drawn patients, the patient who recurred first had a higher probability of recurrence. This calculation assumed that the patient with the shorter follow-up recurred. If both patients recurred at the same time, or the non-recurrent patient had shorter follow-up, the probability did not apply to that pair of patients. The second validation component was to compare predicted probability of recurrence versus actual recurrence (i.e. nomogram calibration) on the 996 patients, again using 200 bootstrap re-samples to reduce overfit bias, which would overstate the accuracy of the nomogram. Finally, the third validation component was simply to apply the nomogram to the 322 patients not included in the modeling sample. For these patients, their predicted probability of recurrence was compared with actual follow-up, and the area under the receiver operating characteristic curve for these men was calculated. All statistical analyses were performed using S-Plus software (PC Version 4.0, Redmond Wash.) with additional functions (called Design) (F. E. Harrell, FE. Design: S-Plus function for biostatistical/epidemiologic modeling, testing, estimation, validation, graphics, prediction, and typesetting by storing enhanced model design attributes in the fit, 1994). Programs available from statlib@lib.stat.cmu.edu) added. All P values resulted from use of two-sided statistical tests.

Figure 4:
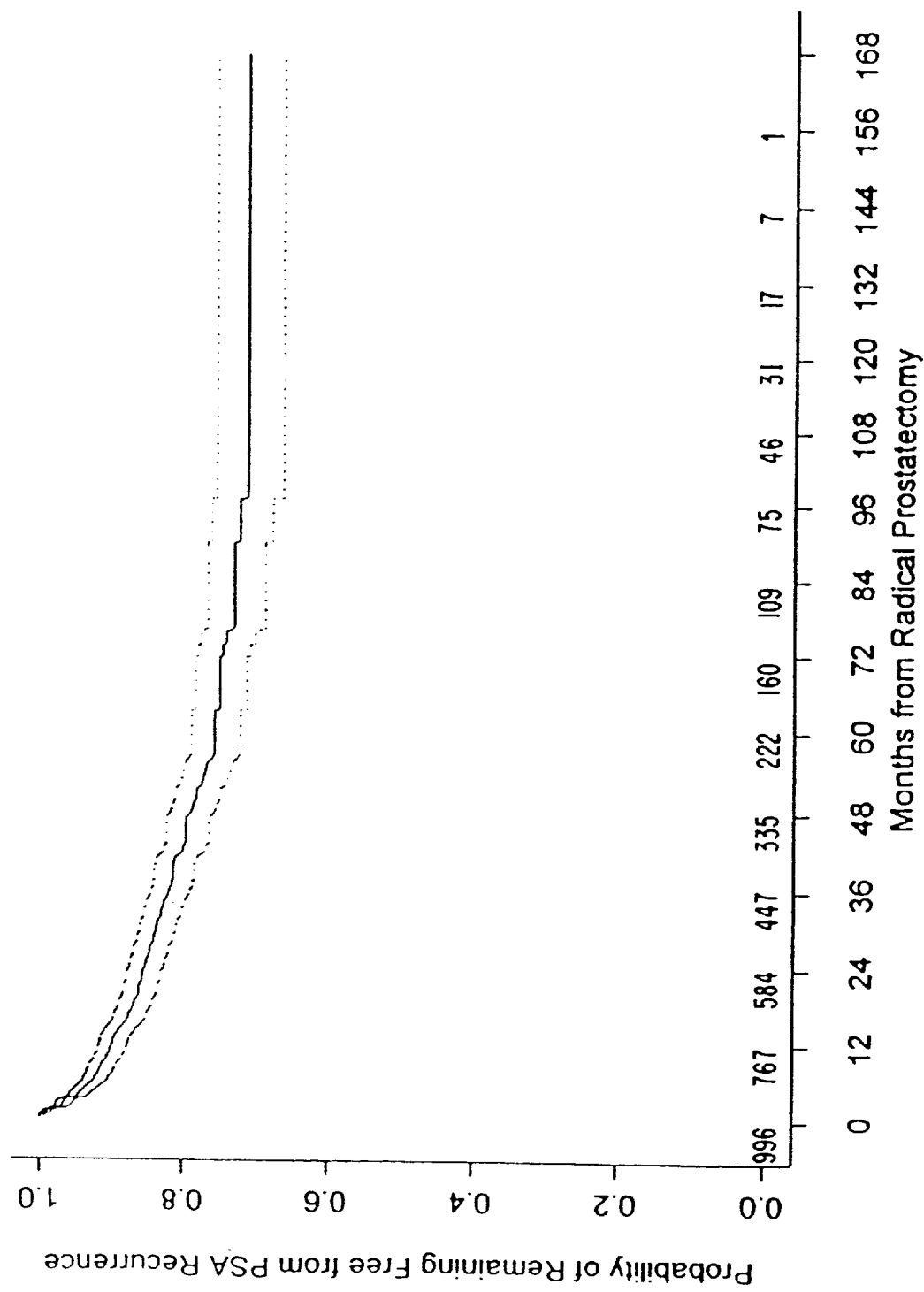
FIG. 4 Graph of overall recurrence-free probabilities following radical prostatectomy for the postoperative nomogram of FIG. 5.

Of the 996 patients available for analysis, 189 had evidence of recurrence of prostate cancer following radical prostatectomy. For patients without disease recurrence, median follow-up was 37 months (range, 1 to 168 months). There were 222 patients with at least 60 months disease-free follow-up, 109 with 84 months disease-free follow-up, and 31 patients with at least 120 months disease-free follow-up. Overall recurrence-free probability for these patients with clinical stage T1a–T3c N0-1M0 prostate cancer was 75% (95% CI=72%–79%) at 5 years, 73% (95% CI=68%–76%) at 7 years, and 71% (95% Cl=66%–75%) at 10 years. FIG. 4 depicts the Kaplan-Meier estimates of disease free probability with 95% confidence intervals for the 996 patients treated with radical prostatectomy during the period from June 1983 through June 1997. The x-axis depicts months from radical prostatectomy and the y-axis depicts the probability of remaining free from PSA recurrence. Numbers above the months indicate patients at risk for recurrence. Recurrence beyond the 7-year point is rare in this series (O. Dillioglugil et al., Urol. 50:93–99, 1997). No recurrences were observed later than 97 months, but the tail of the curve is retained in FIG. 4 to illustrate follow-up. In the multivariable model, all variables were associated with recurrence ($P<0.01$ for each).

Figure 5:
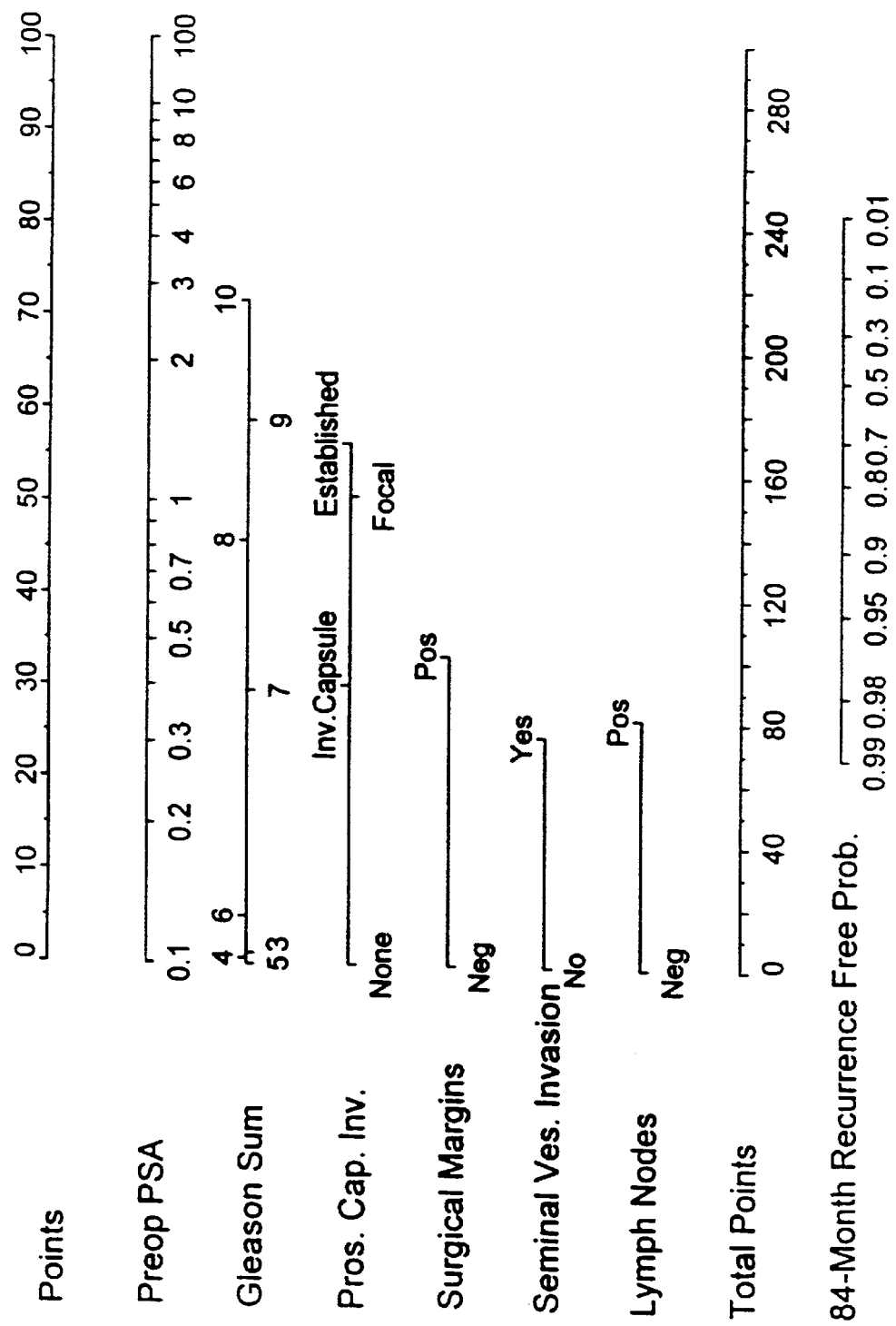
FIG. 5 A third nomogram useful for the postoperative assessment of probability of cancer recurrence following radical prostatectomy.

A nomogram incorporating each of these clinical predictors was constructed based on the Cox model and appears in FIG. 5. The nomogram is used by first locating a patient's position on each predictor variable scale (PSA through lymph node status). Each scale position has corresponding prognostic points (top axis). For example, a PSA of 4 contributes approximately 78 points; this is determined by comparing the location of the 4 value on the PSA axis to the "Points" scale above and drawing a vertical line between the 2 axes. The point values for all predictor variables are determined in a similar manner and are then summed to arrive at a Total Points value. This value is plotted on the Total Points axis (second from the bottom). A vertical line drawn from the Total Points axis straight down to the 84-Month PSA Progression-Free Survival axis will indicate the patient's probability of remaining free from cancer recurrence for 7 years assuming he remains alive.

The nomogram of FIG. 5 was evaluated for its ability to discriminate among patients' risk of recurrence. This was measured as the area under the receiver operating characteristic curve for censored data. This area represents the probability that, when two patients are randomly selected, the patient with the worse prognosis (from the nomogram) will recur before the other patient. This measure can range from 0.5 (a coin toss) to 1.0 (perfect ability to discriminate). Using the original 996 patients who were modeled for the nomogram, the area was calculated to be 0.88.

To derive an estimate of expected performance of the nomogram against new patients, bootstrapping was performed, a statistical method in which sampling, nomogram building, and nomogram evaluation are repeated a large number of times (B. Efron et al., An Introduction to the Bootstrap. New York, N.Y., Chapman and Hall, 1993). This approach simulates the presentation of new patients to the nomogram. With the use of bootstrapping, performance of the nomogram was essentially unchanged, with an area under the receiver operating characteristic curve of 0.88. A decrease in accuracy was expected. However, finding no decrease suggests that the nomogram should perform with similar accuracy in additional, similar patient populations.

Figure 6:
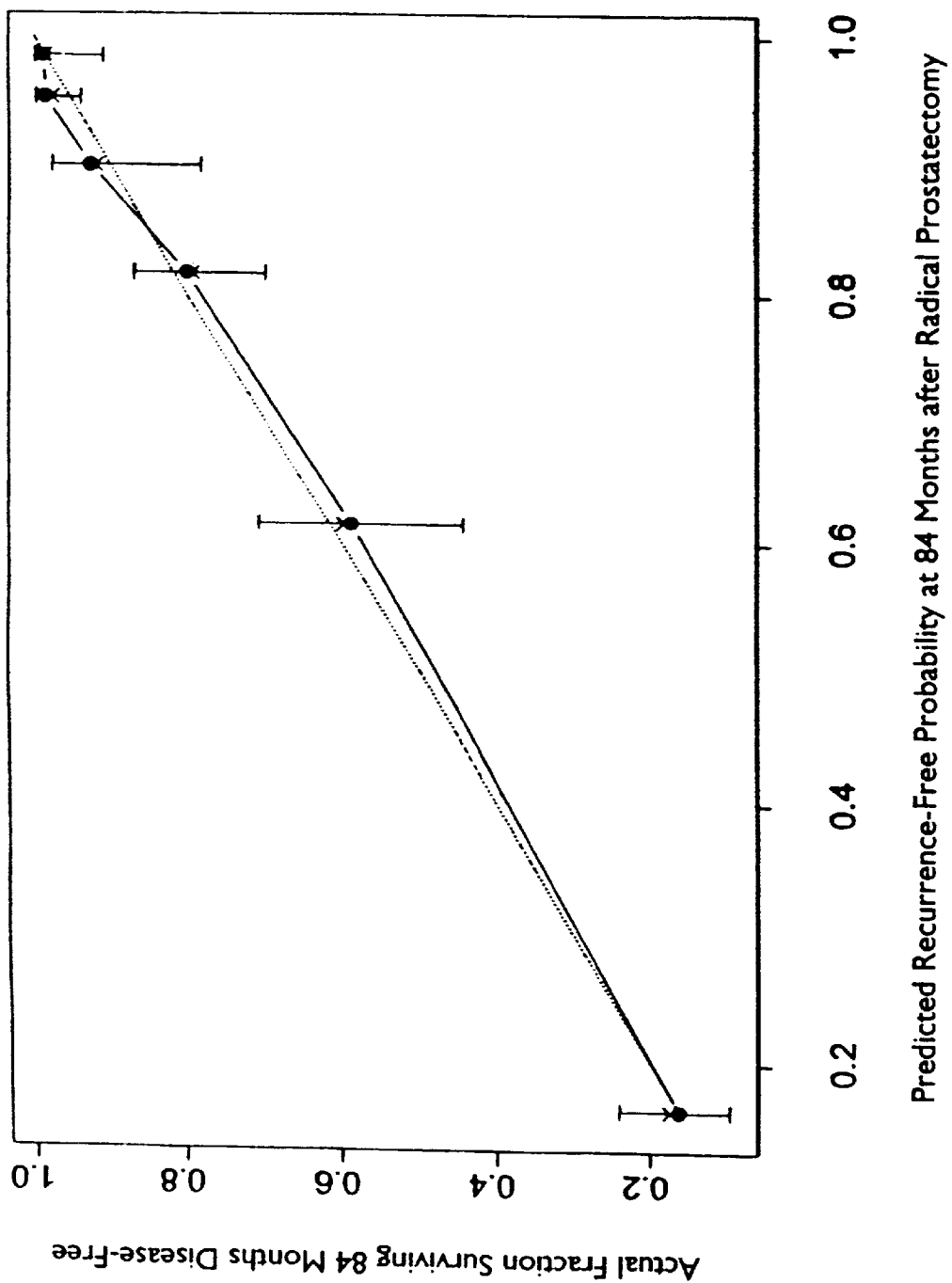
FIG. 6 Comparison of model predictions of FIG. 5 with actual outcome.

FIG. 6 is a calibration of the nomogram of FIG. 5 which illustrates how the predictions from the nomogram compare with actual outcomes for the 996 patients. The x-axis is the prediction calculated with use of the nomogram (predicted recurrence-free probability at 84 months after radical prostatectomy) and the y-axis is the actual freedom from cancer recurrence for the patients (actual fraction surviving 84 months disease-free). The dashed line represents the performance of an ideal nomogram, in which predicted outcome perfectly corresponds with actual outcome. The post-operative nomogram performance is plotted as the solid line that connects the dots, corresponding to sub-cohorts (based on predicted risk) within the dataset. Because the dots are relatively close to the dashed line, the predictions calculated with use of the nomogram approximate the actual outcomes. The X's indicate bootstrap-corrected estimates of the predicted freedom from disease recurrence, which are more appropriate estimates of actual freedom from recurrence. Most of the X's are very close to the dots, indicating that the predictions based on use of the nomogram and modeled data (the dots) are near that expected from use of the new data (the X's). The vertical bars in FIG. 6 indicate 95% confidence intervals based on the bootstrap analysis. In general, the performance of the nomogram appears to be within 10% of actual outcome, and possibly slightly more accurate at very high levels of predicted probability.

As a final method of validation, the probability of 7-year recurrence was predicted for the separate sample of 322 patients. Of these men, 20 had disease recurrence. The predictions made with use of the nomogram were compared with actual outcomes, and the area under the receiver operating characteristic curve was calculated and found to be 0.89.

The disadvantage of the probability approach of the present invention over the previously-used relative risk approach is that when reporting a probability the point in time must be specified. Too early of a time point (e.g. probability of recurring within 2 years) loses clinical usefulness by being inconclusive. Too late of a time point has the disadvantage of potentially being estimated when few patients in the series are at risk that may result in low precision. In the present study, a time point of 84 months was selected in attempt to balance these concerns. Recurrence by PSA is very rare after 84 months, which provides support for judging whether surgery is effective, yet 109 patients remained at risk for recurrence in the present model at 84 months, such that the estimate of the probability at that time may remain reasonably stable.

The present invention differs from those previously published in its methods of validation and assessment. The previous work by Partin and Bauer illustrate the extreme difficulty in validating a survival model. They both produced Kaplan-Meier estimates for the risk strata using validation cohorts, but probably due to small sizes of the cohorts, neither study was able to report all pairwise differences among the strata (i.e. each strata being different from each other strata). The present invention enhances the efficiency of validation and assessment in two ways. First, bootstrapping was employed (B. Efron et al., An Introduction to the Bootstrap. New York, N.Y., Chapman and Hall, 1993) so that each patient could legitimately be used for both model development and model assessment. This more fully utilizes the dataset at hand than does the approach of dividing up the dataset into strata. Second, an overall measure of the ability of the model of the present invention to discriminate among the individual patient's risk of recurrence was reported. In this manner, one can avoid having to form strata that combine patients who are at varying levels of risk into the same risk group. Instead, the discrimination measure of the present invention (area under the receiver operating characteristic curve for censored data) compares each pair of patients and a quantifies the degree to which the model was able to rank those patients. Moreover, the present invention bootstraps the discrimination measure to obtain a reasonable estimate of expected discrimination ability on future data. As two further points of difference with previous studies, the present invention includes patients with clinical stage T3b and T3c disease and utilizes relatively large (N=996 for derivation andN=322 for validation) datasets.

In addition to potentially comforting the patient who is at low probability of recurring, the nomogram of FIG. 5 also has several important uses involving clinical trials. First, it is useful in identifying patients who are appropriate for a clinical trial. The nomogram provides the patient and clinician with the patient's baseline probability of recurrence and together they can decide whether adjuvant therapy is necessary and worth the side effects. Second, as an extension to the first use, the nomogram is potentially able to quantify the expected benefit relative to the baseline risk. A patient at very low risk for recurrence may not have much to gain from a new treatment (R. M. Califf et al., American Heart J 133(6): 630–639, 1992; W. A. Knaus et al., JAMA 270(10):1233–1241, 1993; W. A. Knaus et al., Theor Surg 9:20–27, 1994). In conjunction with the expected efficacy of adjuvant therapy, the nomogram allows quantification of this potential net gain. This is useful even after a clinical trial demonstrates superiority of one treatment over another. The reason for this is that the degree of benefit could be highly variable among patients who are at different baseline risks (R. M. Califf et al., American Heart J 133(6):630–639, 1992). Third, the nomogram can be used to verify the effectiveness of randomization (W. A. Knaus et al., JAMA 270(10):1233–1241, 1993; W. A. Knaus et al., Theor Surg 9:20–27, 1994; W. A. Knaus et al., Crit Care Med 24(1): 46–56, 1996). Treatment arms should have very similar average baseline risks. Fourth, the nomogram may make it possible to reduce the sample sizes of clinical trials for adjuvant therapies (W. A. Knaus et al., Theor Surg 9:20–27, 1994; W. A. Knaus et al., Crit Care Med 24(1): 46–56, 1996). A typical multivariable analysis consumes several degrees of freedom to adjust for potential effects of confounding variables. In other words, part of the sample size requirement for a new trial is associated with estimating the effect of the new therapy, and part is associated with adjusting for the effects of the patient's baseline variables. By collapsing the effects of several baseline variables into an overall recurrence risk (which consumes fewer degrees of freedom than the individual components), a smaller sample is needed because of a smaller demand placed on the trial data to be able to adjust for baseline differences in the treatment arms. Fifth, a uniform method of patient description would help to facilitate comparisons across studies (W.A. Knaus et al., Crit Care Med 24(1): 46–56, 1996). Typical studies report univariable tables of each baseline variable that do not illustrate potential differences in their joint distribution, which the nomogram would consider.

Other possible uses of the nomogram include facilitating the search for a new marker of eventual recurrence following surgery for prostate cancer. Analogous to the clinical trial use above, the sample size requirements to evaluate whether a new marker contributes to the prognostic ability of existing markers are reduced. The nomogram collapses the ability of the previous markers into an overall risk measure which requires a smaller sample size for adjustment, which in turn reduces the overall sample size requirement and thus the number of patients who need to have their new marker measured. Another major use of the nomogram is related to the desire to provide cost effective treatment for society (W. A. Knaus et al., JAMA 270(10):1233–1241, 1993; W. A. Knaus et al., Science 254:389–394, 1991). By quantifying the expected benefit a patient is to receive from a potential treatment and incorporating its cost, a calculation is facilitated as to whether a treatment's expected benefit is worth its expected cost. The purpose here is not to deny the treatment to the patient but instead decide whether the treatment is cost effective from society's point of view (i.e., whether it should be reimbursable).

In addition to serving as a prognostic tool, the nomogram in FIG. 5 is useful for interpreting the underlying Cox model. For example, it appears that PSA is very influential across its spectrum. Also, the nomogram assigns points for the levels of prostatic capsular invasion consistent with degree of tumor spread. Similarly, positive margins, seminal vesicle invasion, and positive lymph nodes each increase the number of points the patient receives towards recurrence. However, the point assignment for Gleason sum appears counter-intuitive (e.g., sum=3 worse than sum=4 worse than sum=5), but these differences reflect variations in coefficient estimates and are not statistically significant (two-sided $P>0.05$). Furthermore, it is important to consider possible changes in other variables (e.g., PSA) when comparing points across levels of a single variable (e.g., seminal vesicle invasion) since patients who differ on one axis are likely to differ on another axis and not be held constant which the eye assumes when comparing across axes. The Cox model coefficients, and therefore the resulting nomogram, look very similar when only the complete records (without imputing) are modeled (data not shown).

The postoperative nomogram of FIG. 5 has certain limitations. The area under the receiver operating characteristic curve on the validation sample was 0.89, while the bootstrap corrected estimate on the original sample was 0.88. Thus, in 11%–12% of patient pairs, the patient with the better prognosis actually recurred first. Also, with respect to accuracy, the confidence intervals at the various predicted probabilities of recurrence (FIG. 6) are somewhat wide, at some levels as much as plus or minus 10%. For the individual patient, this level of error is difficult to interpret since a single patient will either recur or not. One way to apply the nomogram is to say, "Mr. X, if we had 100 men exactly like you, we would expect between <lower confidence limit> and <upper confidence limit> to remain free of their disease for 7 years, assuming they did not die of something else first, and recurrence by PSA after 7 years is rare."

Data from a single surgeon was modeled, and all data came from the same institution. Most of the patients were Caucasian, although others have found no effect of race in multivariable recurrence models prior to variable selection after controlling for fewer pathologic criteria [$P=0.083$ in J. W. Moul et al., J Urol 155:1667–1673, 1996, $P=0.054$ in J. J. Bauer et al., Cancer 79(5):952–962, 1997, not shown in J. J. Bauer et al., J. Urol 159:929–933, 1998]. Although the validation was performed on data that had been obtained from different surgeons and accrued more recently than the data in the nomogram, there may be subtle commonalties among them. In addition, a single expert pathologist performed all pathological assessment. The accuracy of the nomogram in the wider medical community assumes comparable grading accuracy by other pathologists. Further, the applicability of the nomogram assumes that the probability of cancer control after radical prostatectomy is similar when surgeons at other institutions perform the surgery. In fact, there may be substantial variations in outcome, partially due to technical aspects of the operation as measured, for example, by the rate of positive surgical margins.

Nonetheless, the nomogram of FIG. 5 that allows one to predict, from the serum PSA, level of prostatic capsular invasion, specimen Gleason sum, surgical margin status, seminal vesicle invasion, and lymph node status, the probability of cancer recurrence after radical prostatectomy for prostate cancer. The nomogram combines readily available factors and may assist the physician and patient in deciding whether or not adjuvant therapy is an acceptable treatment option. It may also be useful in the design of adjuvant treatment protocols.

Accordingly, one embodiment of this invention is directed to a postoperative method for predicting probability of recurrence of prostatic cancer in a patient who has previously undergone a radical prostatectomy comprising: correlating a selected set of clinical and pathological factors determined for each of a plurality of persons previously diagnosed with prostatic cancer with the incidence of recurrence of prostatic cancer for each person of said plurality to generate a functional representation of the correlation, wherein said selected set of factors comprises one or more of the following: (1) preoperative PSA level; (2) specimen Gleason sum; (3) prostatic capsular invasion level; (4) surgical margin status; (5) presence of seminal vesicle invasion; and (6) lymph node status, wherein said plurality of persons comprises men having undergone radical prostatectomy; and matching an identical set of factors determined from the patient to the functional representation to predict the probability of recurrence of prostatic cancer for the patient.

In a preferred embodiment, the plurality of persons comprises men diagnosed with prostatic cancer and treated with radical retropubic prostatectomy. Preferably, these men underwent surgery between June 1983 and June 1997 at The Methodist Hospital. As will be clear to one of skill in the art, other suitable populations may be used.

In a preferred postoperative embodiment, surgical margin status is reported as negative or positive. Alternatively, surgical margin status may be reported as negative, close or positive. Prostatic capsular invasion level is preferably reported as none, invading the capsule, focal or established.

Seminal vesicle involvement or invasion is preferably reported as yes or no. Alternatively, it may be ranked as positive or negative, or absent or present. If present, seminal vesicle involvement can be alternatively classified by level as Types I, II, I+II, or III (M. Ohori et al., Am J Surg Pathol 17:1252–1261, 1993). In yet another embodiment, seminal vesicle invasion, if present, may be alternatively ranked by level as type I, II, or III (T. M. Wheeler, Urol Clin North Am 16:623–634, 1989; M. Ohori et al., Am J Surg Pathol 17:1252–1261, 1993). Lymph node status is preferably recorded as either positive or negative. In alternative embodiments, one or more subgroups of any one or more of these factors may be excluded.

In yet another embodiment, the selected set of clinical and pathological factors may further include one or more of the following: the volume of cancer (total tumor volume), the zone of the prostate where the tumor is found (zone of location of the cancer), level of extraprostatic extension, p53, Ki-67, p27, DNA ploidy status, clinical stage, lymphovascular invasion, and other routinely determined pathological factors. (D. R. Greene et al., J Urol 146:1069–1076, 1991; D. R. Greene et al., Campbell's Urology, vol. 1, 6th ed, W. B. Saunders Co., 1992; M. Ohori et al., Prostate 23 (4):271–281, 1993; A. M. F. Stapleton, et al., Cancer 82 (1): 168–75, 1998; R. M. Yang et al., J Urol 159 (3):941–5, 1998).

Level of extraprostatic extension may be evaluated as negative, level 1, level 2, level 3 focal, or level 3 established (Stamey et al., J Urol 139:1235–1241, 1998; Rosen et al., J Urol 148:331–337, 1992). Alternatively, level of extraprostatic extension may be evaluated as negative, level 1, level 2 or level 3 focal. Alternatively, level of extraprostatic extension may be evaluated as level 0 or 1 (no invasion of the capsule or extension outside of the prostate), level 2 (invasion into but not through the capsule), level 3F (focal microscopic extension through the capsule comprising no more than two high power fields on all histologic sections), or level 3E (established extension through the capsule more extensive than level 3F) (T. M. Wheeler et al., Hum Pathol 29(8), 1998, in press; M. Ohori et al., Am J Surg Pathol 17:1252–1261, 1993; D. R. Greene et al., J Urol 146:1069–1076, 1991; D. R. Greene et al., Campbell's Urology, vol. 1, 6th ed. W. B. Saunders Co. 342–393, 1992; D. R. Greene et al., Br. J Urol. 68:499–509, 1991; M. Ohori et al., Prostate 23(4):271–281, 1993).

The probability of recurrence of prostate cancer of the preferred embodiment is defined as the probability of remaining free of prostatic cancer seven years following radical prostatectomy. Recurrence maybe characterized as an increased serum PSA level or as positive biopsy, bone scan, or other suitable imaging test or clinical parameter. Alternatively recurrence may be characterized as a positive biopsy, bone scan or the initiation or application of further treatment for prostate cancer because of the high probability of subsequent recurrence of the cancer.

In a preferred embodiment, the functional representation is a nomogram. The nomogram may be generated with a Cox proportional hazards regression model. (D. R. Cox, Regression models and life tables (with discussion), Journal of the Royal Statistical Society B34: 187–220,1972). Alternatively, the nomogram may be generated with a neural network model. (D. E. Rumelhart et al., Parallel Distributed Processing: Exploration in the Microstructure of Cognition Volume 1. Foundations. Cambridge, Mass.: The MIT Press, 1986). In still another embodiment, the nomogram is generated with a recursive partitioning model (L. Breiman et al., Classification and Regression Trees. Monterey, Calif.: Wadsworth and Brooks/Cole, 1984). Other models known to those skilled in the art may alternatively be used.

Still another embodiment of the invention is directed to a nomogram for determining a postoperative probability of prostatic cancer recurrence as depicted or represented in FIG. 5.

Figures 1, 7:
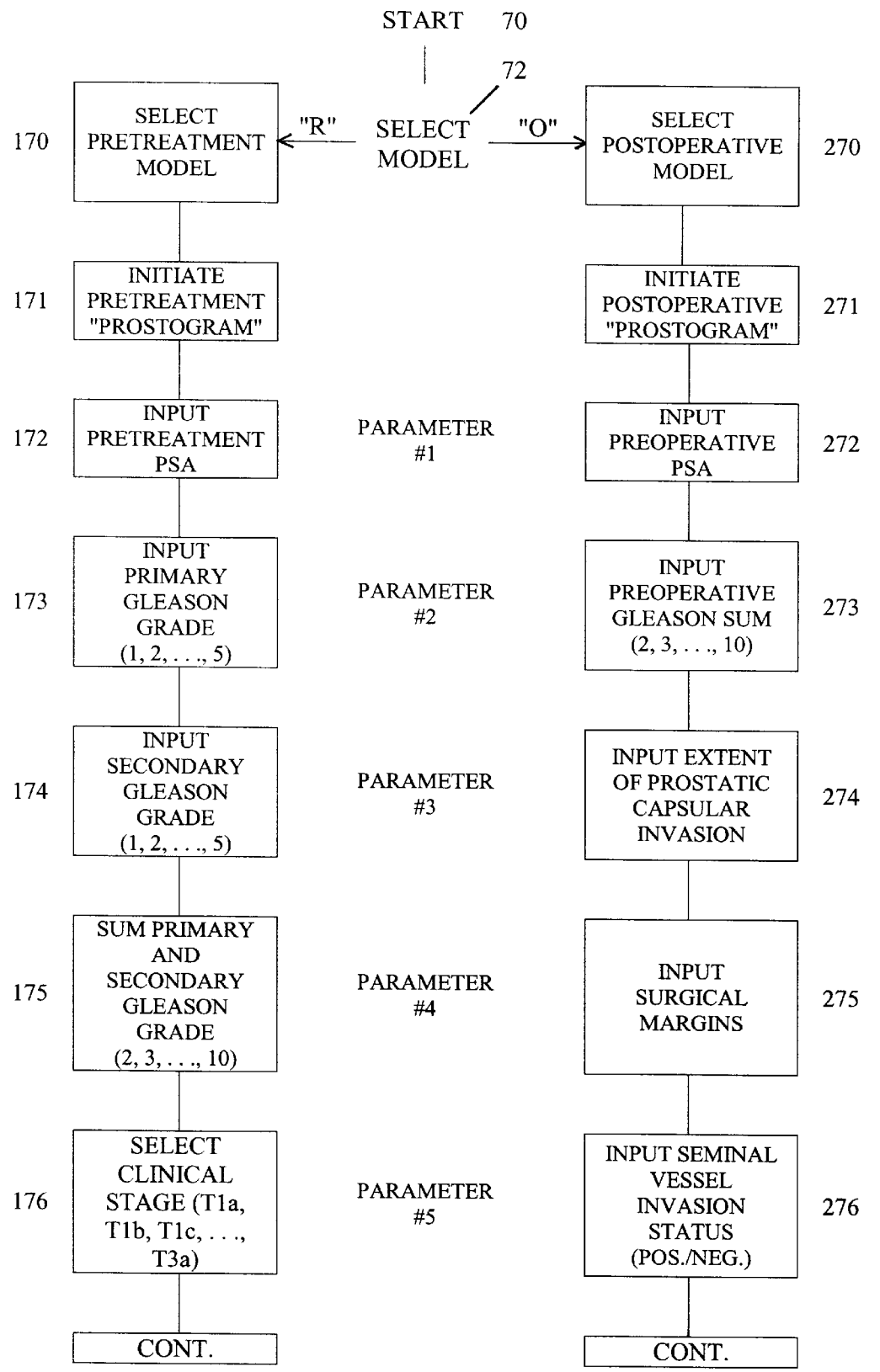

Another embodiment of the invention is directed to software logic useful in, for example, hand-held compters such as a Palm Pilot™. A software logic flow chart is depicted in FIG. 7.

Another embodiment of the invention is directed to a method to predict a postoperative prognosis in a patient following radical prostatectomy, comprising matching a patient-specific set of clinical and pathological factors comprising the patient's preoperative PSA level, specimen Gleason sum, prostatic capsular invasion level, surgical margin status, presence of seminal vesicle invasion, and lymph node status to the nomogram depicted in FIG. 5 and determining the prognosis of the patient.

Still another embodiment of the invention is directed to a method for determining a need for an adjuvant therapy in a patient following radical pro statectomy comprising the steps of determining a set of clinical and pathological factors on the patient, the set of factors comprising the patient's preoperative PSA level, specimen Gleason sum, prostatic capsular invasion level, surgical margin status, presence of seminal vesicle invasion, and lymph node status; and matching the set of factors to the nomogram depicted in FIG. 5 to determine whether the adjuvant therapy is needed in view of the probability of recurrence. The adjuvant therapy may comprise radiotherapy, chemotherapy, hormonal therapy (such as anti-androgen hormonal therapy), cryotherapy, interstitial radioactive seed implantation, external beam irradiation, hyperthermia, gene therapy, cellular therapy, tumor vaccine, or systemically delivered biologic agents or pharmaceuticals.

Another embodiment of the invention is directed to an apparatus for predicting probability of disease recurrence in a patient with pro static cancer following a radical prostatectomy, wherein the apparatus comprises a correlation of clinical and pathological factors determined for each of a plurality of persons previously diagnosed with prostatic cancer and having been treated by radical prostatectomy with incidence of recurrence of prostatic cancer for each person of said plurality of persons wherein said selected set of factors comprises preoperative PSA level, specimen Gleason sum, prostatic capsular invasion level, surgical margin status, presence of seminal vesicle invasion, and lymph node status; and a means for matching an identical set of factors determined from the patient diagnosed as having prostatic cancer to the correlation to predict the probability of recurrence of prostatic cancer in the patient following radical prostatectomy.

Another embodiment of the invention is directed to a nomogram for the graphic representation of a probability that a patient with prostate cancer will remain free of disease following radical prostatectomy comprising a set of indicia on a solid support, the indicia comprising a preoperative PSA level line, specimen Gleason sum line, a prostatic capsular invasion level line, a surgical margin status line, a presence of seminal vesicle invasion line, a lymph node status line, a points line, a total points line and a predictor line, wherein said preoperative PSA level line, specimen Gleason sum line, prostatic capsular invasion level line, surgical margin status line, presence of seminal vesicle invasion line, and lymph node status line each have values on a scale which can be correlated with values on a scale on the points line, and wherein said total points line has values on a scale which may be correlated with values on a scale on the predictor line, such that the value of each of the points correlating with the patient's preoperative PSA level, specimen Gleason sum, prostatic capsular invasion level, surgical margin status, presence of seminal vesicle invasion, and lymph node status can be added together to yield a total points value, and the total points value can be correlated with the predictor line to predict the probability of recurrence. The solid support may assume any appropriate form such as, for example, a laminated card. Any other suitable representation, picture, depiction or exemplification may be used.

EXAMPLES

Figures 2, 7:
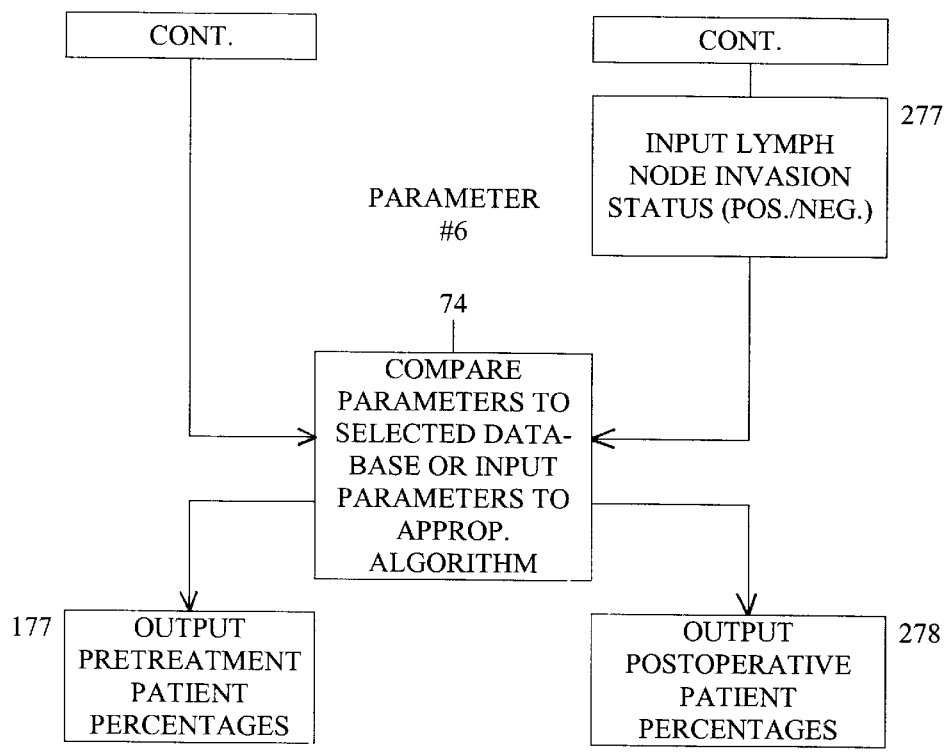

The invention is further clarified by a consideration of the following example, which is intended to be purely exemplary of the use of the invention. Referring to FIGS. 7-1 and 7-2, a flow chart depicts the software logic which may be employed to implement and utilize the invention on a computer, such as a Palm Pilot™ handheld computer, laptop computer or other personal computer. Once the program is initiated (step 70), the operator selects between two models for utilizing the invention (step 72). The model selected will depend on the needs of the operator and the condition of the patient. If the Pretreatment model (step 170) is selected, the operator will utilize the invention to obtain information concerning a prognosis for patient survival and for the spread of the cancer withing the patient. If instead, the Postoperative model (step 270) is selected, the operator will utilize the invention to obtain information concerning the prognosis for patient survival after surgery.

Considering first the Pretreatment model (step 170), selection of this model prompts the software to initiate the generation of a pretreatment prostogram (step 171). Essentially, this creates a template for receiving information necessary to generate results from the pretreatment model. The pretreatment prostogram will seek input of the pretreatment PSA (step 172), the Primary Gleason Grade (step 173), and the Secondary Gleason Grade (step 174). Each Gleason Grade is selected from a set of integer values between 1 and 5. Once this data is entered into the prostogram program, the Gleason Sum (i.e. the Primary Gleason Grade plus the Secondary Gleason Grade) is generated in step 175). Because each Gleason Grade has a value between 1 and 5, the Gleason Sum has an integer value between 2 and 10. Finally, the Clinical Stage is entered into the prostogram program at step 176. Examples of the Clinical Stages are provided in Table 1, discussed above.

The information may be entered into the program in a variety of ways. For example, the values may be keyed in by means of a keyboard or other alphanumeric data entry device. Alternatively, the program maybe designed to present lists of options from which the operator may select desired data values with a light pen or other electro-optic or electromagnetic device. The order in which the data is entered is relatively flexible. However, both the Primary Gleason Grade and the Secondary Gleason Grade are entered to generate the Gleason Sum.

Once the desired parameters have been input to the prostogram program, the parameters may be compared to a data base defining the geometric and mathematical relationships between the elements of the nomogram (step 74). Alternatively, the parameters may be processed by a series of algorithms defining the relationship the geometric and mathematical relationships between the elements of the nomogram. Because the nomogram defines the geometric and mathematical relationships between a set of parallel scales, these relationships may also be defined in terms of a data base defining the relationships between the scales, algorithms defining the relationships between the scales or a combination of both.

Once the parameters have been entered and compared to the nomogram database or algorithms, or both, an output of patient pretreatment percentages may be generated (step 177). For example, the output may consist of a screen defining the confidence interval for the particular results and various patient percentages, including: the patient's five-year recurrence free, survival probability; the probability that the cancer will be confined to the prostrate; the probability of prostatic capsular invasion; the probability of seminal vessel invasion; and the probability of lymph node invasion.

If, however, the Postoperative model (step 270) is selected, this model prompts the software to initiate the generation of a postoperative prostogram (step 271). Essentially, this again creates a template for receiving information necessary to generate results from the postoperative model. The postoperative prostogram will seek input of the pretreatment PSA (step 272), the Gleason Sum (step 273), an input identifying the extent of prostatic capsular invasion (step 274); an input identifying the surgical margins (step 275); an input identifying the status of seminal vessel invasion (step 276); and an input identifying the status of lymph node invasion (step 277). The Gleason Sum may either be entered automatically if pretreatment calculation were conducted first, or the Gleason Sum may be separately calculated by the operator based on the Primary and Secondary Gleason Grades. The extent of prostatic capsular invasion may be measured and entered in various ways. For example, a screen menu may be presented offering the operator a selection between various "extent" identifiers, such as: None, Invading the Capsule, Focal Invasion, or Established within the Capsule. A much simpler menu may be used to enter the surgical margin, seminal vessel invasion, and lymph node invasion parameters. The menu may consist simply of a choice between "Negative" and "Positive."

Once the desired postoperative parameters have been input to the prostogram program, these parameters may then be compared to a data base defining the geometric and mathematical relationships between the elements of the nomogram (step 74). Alternatively, the parameters may be processed by a series of algorithms defining the relationship the geometric and mathematical relationships between the elements of the nomogram. Because the nomogram defines the geometric and mathematical relationships between a set of parallel scales, these relationships may also be defined in terms of a data base defining the relationships between the scales, algorithms defining the relationships between the scales or a combination of both.

Once the postoperative parameters have been entered and compared to the nomogram database or algorithms, or both, an output of patient postoperative percentages may be generated (step 277). For example, the output may consist of a screen defining the confidence interval for the particular results and various patient percentages, including: the patient's seven-year recurrence free, survival probability.

Other embodiments and uses of the invention will be apparent to those skilled in the art from consideration of the specification and practice of the invention disclosed herein. All documents, including U.S. patents and applications disclosed herein and specifically U.S. provisional patent application Ser. No. 60/051,428, and U.S. patent application Ser. No. 09/104,218, are specifically incorporated herein by reference. The specification and example should be considered exemplary only with the true scope and spirit of the invention indicated by the following claims.

What is claimed is:

1. An apparatus for predicting a quantitative probability of disease recurrence in a patient with prostatic cancer following an identified therapy, wherein the apparatus comprises:
   a correlation of factors determined for each of a plurality of persons previously diagnosed with prostatic cancer and having been treated by said identified therapy with incidence of recurrence of prostatic cancer for each person of said plurality of persons, wherein said selected set of factors comprises two or more factors selected from the group consisting of pretreatment PSA level, combined Gleason grade, specimen Gleason sum, clinical stage, surgical margin status, prostatic capsular invasion maximum cancer length in a core, total length of cancer in the biopsy cores, percent of cores positive level, extraprostatic extension, level of extraprostatic extension, apoptotic index, percent of cancer in one or more cores, percent of high grade cancer in one or more cores, total tumor volume, zone of location of the cancer, presence of seminal vesicle invasion, type of seminal vesicle invasion, p53, Ki-67, p27, DNA ploidy status, lymph node status, and lymphovascular invasion; and
   a processor, wherein said processor compares an identical set of factors determined from the patient diagnosed as having prostatic cancer to the correlation to predict the quantitative probability of recurrence of prostatic cancer in the patient following said identified therapy.

2. The apparatus of claim 1 wherein said identified therapy is selected from the group consisting of radical prostatectomy, radiation therapy, brachytherapy, hormonal therapy, cryotherapy, chemotherapy and combinations thereof.

3. The apparatus of claim 1 wherein said apparatus comprises a nomogram.

4. The apparatus of claim 3 wherein said nomogram is disposed on a laminated card.

5. The apparatus of claim 3 wherein said nomogram comprises a graphic representation.

6. The apparatus of claim 3 wherein said nomogram is stored in a memory.

7. The apparatus of claim 6 wherein said memory is selected from the group consisting of random access memory, read-only memory, disk, virtual memory, processor, and the like.

8. The apparatus of claim 3 wherein said nomogram is stored in a database.

9. The apparatus of claim 8 wherein said database is accessible by multiple users.

10. The apparatus of claim 3 further comprising a storage mechanism, wherein said storage mechanism stores said nomogram; an input device that inputs said identical set of factors determined from said patient into said apparatus; and a display mechanism, wherein said display mechanism displays said quantitive probability of recurrence of prostatic cancer.

11. The apparatus of claim 10, wherein said storage mechanism is selected from the group consisting of random access memory, read-only memory, a disk, virtual memory, a database, and a processor.

12. The apparatus of claim 10, wherein said input device is selected from the group consisting of a keypad, a keyboard, stored data, a touch screen, a voice activated system, a downloadable program, downloadable data, a digital interface, a hand-held device, and an infra-red signal device.

13. The apparatus of claim 10, wherein said display mechanism is selected from the group consisting of a computer monitor, a cathode ray tub (CRT), a digital screen, a light-emitting diode (LED), a liquid crystal display (LCD), an X-ray, a compressed digitized image, a video image, and a hand-held device.

14. The apparatus of claim 1 further comprising a display that displays said quantitive probability of recurrence of prostatic cancer.

15. The apparatus of claim 14 wherein said display is separated from said processor such that said display receives said quantitative probability of recurrence of prostatic cancer.

16. The apparatus of claim 1 further comprising a database, wherein said database
   stores said correlation of factors and is accessible by said processor.

17. The apparatus of claim 1 further comprising an input device that inputs said identical set of factors determined from the patient diagnosed as having prostatic cancer into said apparatus.

18. The apparatus of claim 14 wherein said input device stores said identical set of factors in a storage mechanism that is accessible by said processor.

19. The apparatus of claim 1 further comprising a transmission medium for transmitting said selected set of factors.

20. The apparatus of claim 19 wherein said transmission medium is coupled to said processor and said correlation of factors.

21. The apparatus of claim 1 further comprising a transmission medium for transmitting said identical set of factors determined from the patient diagnosed as having prostatic cancer.

22. The apparatus of claim 21 wherein said transmission medium is coupled to said
   processor and said correlation of factors.

23. The apparatus of claim 1 wherein said processor is a multi-purpose or a dedicated processor.

24. The apparatus of claim 1 wherein said processor includes an object oriented program having libraries, said libraries storing said correlation of factors.

25. An apparatus for predicting a quantitative probability of disease recurrence in a patient with prostatic cancer following a radical prostatectomy, wherein the apparatus comprises:
   a correlation of clinical and pathological factors determined for each of a plurality of persons previously diagnosed with prostatic cancer and having been treated by radical prostatectomy with incidence of recurrence of prostatic cancer for each person of said plurality of persons wherein said selected set of factors comprises specimen Gleason sum, surgical margin status, presence of seminal vesicle invasion, and lymph node status; and a processor, wherein said processor compares an identical set of factors determined from the patient diagnosed as having prostatic cancer to the correlation to predict the quantitative probability of recurrence of prostatic cancer in the patient following radical prostatectomy.

26. A nomogram for the graphic representation of a quantitative probability that a patient with prostate cancer will remain free of disease following radical prostatectomy comprising:

a plurality of scales and a solid support, the plurality of scales being disposed on said support and comprising a specimen Gleason sum scale, a surgical margin status scale, a presence of seminal vesicle invasion scale, a lymph node status scale, a points scale, a total points scale and a predictor scale, wherein said specimen Gleason sum scale, surgical margin status scale, presence of seminal vesicle invasion scale, and lymph node status scale each have values on said scales, and wherein said specimen Gleason sum scale, said surgical margin status scale, said presence of seminal vesicle invasion scale, and said lymph node status scale are disposed on said solid support with respect to the points scale so that each of said values on said specimen Gleason sum scale, said surgical margin status scale, said presence of seminal vesicle invasion scale, and said lymph node status scale can be correlated with values on the points scale, and wherein said total points scale has values on said total points scale and wherein said total points scale is disposed on said solid support with respect to the predictor scale so that said values on said total points scale may be correlated with values on the predictor scale, such that the values on the points scale correlating with the patient's specimen Gleason sum, surgical margin status, presence of seminal vesicle invasion, and lymph node status can be added together to yield a total points value, and the total points value can be correlated with the predictor scale to predict the quantitative probability of recurrence.

27. The nomogram of claim 26 wherein said nomogram is stored in a memory.

28. The nomogram of claim 26 further comprising a display that displays said nomogram.

29. A method to predict a postoperative prognosis in a patient following radical prostatectomy, comprising:

determining a set of factors comprising the patient's specimen Gleason sum, surgical margin status, presence of seminal vesicle invasion, and lymph node status; matching the factors to the values on the specimen Gleason sum scale, the surgical margin status scale, the presence of seminal vesicle invasion scale and the lymph node status scale of the nomogram of claim 26;

determining a separate point value for each of said factors;

adding the separate point values together to yield a total points value; and correlating the total points value with a value on the predictor scale of said nomogram to determine the prognosis of the patient.

30. A method for predicting a quantitative probability of recurrence of prostatic cancer in a patient following treatment with an identified therapy comprising the steps of:

correlating a selected set of factors determined for each of a plurality of persons previously diagnosed with prostatic cancer and having been treated by said identified therapy with incidence of recurrence of prostatic cancer for each person of said plurality of persons to generate a functional representation of the correlation, wherein said selected set of factors comprises at least two factors selected from the group consisting of pretreatment PSA level, combined Gleason grade, specimen Gleason sum, clinical stage, surgical margin status, prostatic capsular invasion level, extraprostatic extension, level of extraprostatic extension, apoptotic index, maximum cancer length in a core, total length of cancer in the biopsy cores, percent of cores positive, percent of cancer in one or more cores, percent of high grade cancer in one or more cores, total tumor volume, zone of location of the cancer, presence of seminal vesicle invasion, type of seminal vesicle invasion, p53, Ki-67, p27, DNA ploidy status, lymph node status, and lymphovascular invasion, wherein said functional representation of the correlation comprises a different factor evaluation system for each of said factors, and wherein each of said factor evaluation systems provides a value corresponding with a status of said corresponding factor, which value may be summed with values corresponding to the status of the other factors in the selected set to derive a quantitative probability of recurrence of prostatic cancer following said identified therapy;

determining the status of an identical set of factors for the patient;

applying the status of each of the patient's set of factors to said corresponding factor evaluation system to determine a patient value for each of said factors; and summing the patient's values to derive the quantitative probability of recurrence of prostatic cancer in the patient following said identified therapy.

31. The method of claim 30 wherein each of said factor evaluation systems comprises a scale having values corresponding to status and the step of applying comprises matching the patient's status for each of said factors to its status on the corresponding scale to determine the patient's values for each of said factors.

32. The method of claim 30 wherein the functional representation is a nomogram.

33. The method of claim 30 further comprising the step of displaying the functional representation on a display.

34. The method of claim 30 further comprising the step of inputting said identical set of factors for the patient within input device.

35. The method of claim 30 wherein said correlating step is executed by a processor.

36. The method of claim 30 wherein said determining step is executed by a processor.

37. The method of claim 30 wherein said applying step is executed by a processor.

38. The method of claim 30 wherein said summing step is executed by a processor.

39. The method of claim 30 wherein said correlating step is executed by a virtual computer program.

40. The method of claim 30 wherein said determining step is executed by a virtual computer program.

41. The method of claim 30 wherein said applying step is executed by a virtual computer program.

42. The method of claim 30 wherein said summing step is executed by a virtual computer program.

43. The method of claim 30 wherein said correlating step includes accessing a memory storing said selected set of factors.

44. The method of claim 30 wherein said determining step includes accessing a memory storing said identical set of factors.

45. The method of claim 30 further comprising the step of storing any of said set of factors to a memory.

46. The method of claim 30 further comprising the step of storing any of said set of factors to a database.

47. The method of claim 30 wherein said correlating step includes generating said functional representation and displaying said functional representation on a display.

48. The method of claim 47 wherein said displaying step includes transmitting said functional representation to said display.

49. The method of claim 47 wherein said displaying step includes downloading said functional representation from a source.

50. The method of claim 30 further comprising the step of transmitting said quantitative probability of recurrence of prostatic cancer.

51. The method of claim 30 wherein identified therapy is selected from the group consisting of radical prostatectomy, radiation therapy, brachytherapy, hormonal therapy, cryotherapy, chemotherapy and combinations thereof.

52. A method for predicting a quantitative probability of recurrence of prostatic cancer following radical prostatectomy in a patient diagnosed as having prostatic cancer comprising the steps of:

correlating a selected set of preoperative factors determined for each of a plurality of persons previously diagnosed with prostatic cancer and having been treated by radical prostatectomy with incidence of recurrence of prostatic cancer for each person of said plurality of persons to generate a functional representation of the correlation, wherein said selected set of preoperative factors comprises pretreatment PSA level, combined Gleason grade, clinical stage, and one or more supplemental factors selected from the group consisting of apoptotic index, maximum cancer length in a core, percent of cores positive, percent of cancer in one or more cores, percent of high grade cancer in one or more cores and total length of cancer in the biopsy cores, wherein said functional representation of the correlation comprises a pretreatment PSA level scale, a clinical stage scale, a combined Gleason grade scale, one or more supplemental factor scales for each of said one or more supplemental factors, a points scale, a total points scale, and a predictor scale, and wherein said pretreatment PSA level scale, said clinical stage scale, said combined Gleason grade scale and said one or more supplemental factors scales each have values on said scales which can be correlated with values on the points scale, and wherein said total points scale has values which may be correlated with values on the predictor scale;

determining an identical set of preoperative factors for the patient; matching the patient's pretreatment PSA level to a corresponding value on the pretreatment PSA level scale, and determining a first point value from the corresponding value on the points scale;

matching the patient's combined Gleason grade to a corresponding value on the combined Gleason grade scale, and determining a second point value from the corresponding value on the points scale;

matching the patient's clinical stage to a corresponding value on the clinical stage scale, and determining a third point value from the corresponding value on the points scale;

matching the patient's one or more supplemental factors to one or more corresponding values on the one or more supplemental factor scales to determine one or more supplemental point values on the points scale;

adding the first, second and third and one or more supplemental point values together to get a patient total points value;

matching the patient total points value to a corresponding value on the total points scale; and correlating the corresponding value on the total points scale with a value on the predictor scale to predict the quantitative probability of recurrence of prostatic cancer in the patient following radical prostatectomy.

53. The method of claim 52 wherein said steps are executed on a computer processing device, wherein said computer processing device displays said values to a user.

54. The method of claim 52 wherein said steps are executed on an embedded processor.

55. A postoperative method for predicting a quantitative probability of recurrence of prostatic cancer in a patient who has previously undergone a radical prostatectomy comprising the steps of:

correlating a selected set of factors determined for each of a plurality of persons previously diagnosed with prostatic cancer with incidence of recurrence of prostatic cancer for each person of said plurality to generate a functional representation of the correlation, wherein said selected set of factors comprises specimen Gleason sum, surgical margin status, presence of seminal vesicle invasion, and lymph node status, wherein said plurality of persons comprises men having undergone radical prostatectomy, wherein said functional representation of the correlation comprises a specimen Gleason sum scale, a surgical margin status scale, a presence of seminal vesicle invasion scale, a lymph node status scale, a points scale, a total points scale, and a predictor scale, and wherein said specimen Gleason sum scale, said surgical margin status scale, said presence of seminal vesicle invasion scale, and said lymph node status scale each have values on said scales which can be correlated with values on the points scale, and wherein said total points scale has values on said scale which may be correlated with values on the predictor scale;

determining an identical set of factors for the patient;

matching the patient's specimen Gleason sum to a corresponding value on the specimen Gleason sum scale, and determining a first point value from the corresponding value on the points scale;

matching the patient's surgical margin status to a corresponding value on the surgical margin status scale, and determining a second point value from the corresponding value on the points scale;

matching the patient's presence of seminal vesicle invasion to a corresponding value on the presence of seminal vesicle invasion scale, and determining a third point value from the corresponding value on the points scale;

matching the patient's lymph node status to a corresponding value on the lymph node status scale, and determining a fourth point value from the corresponding value on the points scale;

adding the first, second, third, and fourth point values together to get a patient total points value;

matching the patient total points value to a corresponding value on the total points scale; and correlating the corresponding value on the total points scale with a value on the predictor scale to predict the quantitative probability of recurrence of prostatic cancer for the patient.

56. The method of claim 55 wherein the selected set of factors further comprises one or more supplemental factors selected from the group consisting of total tumor volume, pretreatment PSA, prostatic capsular invasion, zone of location of the cancer, p53, Ki-67, p27, level of extraprostatic extension, DNA ploidy status, type of seminal vesicle invasion, clinical stage and lymphovascular invasion and said functional representation further comprises one or more supplemental factor scales for each of said one or more supplemental factors, said one or more supplemental factor scales each having values on said scales which can be correlated with the values on the points scale, and wherein the method further comprises the steps of:

determining the patient's one or more supplemental factors;

matching the patient's one or more supplemental factors to one or more corresponding values on the one or more supplemental factor scales to determine one or more supplemental point values on the points scale; and adding the one or more supplemental point values to the first, second, third, and fourth point values to determine the patient total points value.

57. The method of claim 55 wherein said steps are executed on a computer processing device, said computer processing device displays said values to a user.

58. The method of claim 55 wherein said steps are executed on an embedded processor.

59. A method of using a computer processor for predicting a quantitative probability of recurrence of prostatic cancer in a patient following treatment with an identified therapy comprising the steps of:

correlating a selected set of factors determined for each of a plurality of persons previously diagnosed with prostatic cancer and having been treated by said identified therapy with incidence of recurrence of prostatic cancer for each person of said plurality of persons to generate a functional representation of the correlation using said computer processor, wherein said selected set of factors comprises at least two factors selected from the group consisting of pretreatment PSA level, combined Gleason grade, specimen Gleason sum, clinical stage, surgical margin status, prostatic capsular invasion level, extraprostatic extension, level of extraprostatic extension, apoptotic index, maximum cancer length in a core, total length of cancer in the biopsy cores, percent of cores positive, percent of cancer in one or more cores, percent of high grade cancer in one or more cores, total tumor volume, zone of location of the cancer, presence of seminal vesicle invasion, type of seminal vesicle invasion, p53, Ki-67, p27, DNA ploidy status, lymph node status, and lymphovascular invasion, wherein said functional representation of the correlation comprises a different factor evaluation system for each of said factors, and wherein each of said factor evaluation systems provides a value corresponding with a status of said corresponding factor, which value may be summed with values corresponding to the status of the other factors in the selected set to derive a quantitative probability of recurrence of prostatic cancer following said identified therapy;

determining the status of an identical set of factors for the patient using said computer processor;

applying the status of each of the patient's set of factors to said corresponding factor evaluation system to determine a patient value for each of said factors using said computer processor; and summing the patient's values to derive the quantitative probability of recurrence of prostatic cancer in the patient following said identified therapy.

60. The method of claim 59 further comprising a memory coupled to said computer processor.

61. The method of claim 59 further comprising an input device coupled to said computer processor.

62. The method of claim 59 further comprising a display coupled to said computer processor, said display receives data from said computer processor.

63. A computerized method for predicting a quantitative probability of recurrence of prostatic cancer in a patient following treatment with an identified therapy comprising the steps of:

correlating a selected set of factors determined for each of a plurality of persons previously diagnosed with prostatic cancer and having been treated by said identified therapy with incidence of recurrence of prostatic cancer for each person of said plurality of persons to generate a functional representation of the correlation, wherein said selected set of factors comprises at least two factors selected from the group consisting of pretreatment PSA level, combined Gleason grade, specimen Gleason sum, clinical stage, surgical margin status, prostatic capsular invasion level, extraprostatic extension, level of extraprostatic extension, apoptotic index, maximum cancer length in a core, total length of cancer in the biopsy cores, percent of cores positive, percent of cancer in one or more cores, percent of high grade cancer in one or more cores, total tumor volume, zone of location of the cancer, presence of seminal vesicle invasion, type of seminal vesicle invasion, p53, Ki-67, p27, DNA ploidy status, lymph node status, and lymphovascular invasion, wherein said functional representation of the correlation comprises a different factor evaluation system for each of said factors, and wherein each of said factor evaluation systems provides a value corresponding with a status of said corresponding factor, which value may be summed with values corresponding to the status of the other factors in the selected set to derive a quantitative probability of recurrence of prostatic cancer following said identified therapy;

determining the status of an identical set of factors for the patient;

applying the status of each of the patient's set of factors to said corresponding factor evaluation system to determine a patient value for each of said factors; and summing the patient's values to derive the quantitative probability of recurrence of prostatic cancer in the patient following said identified therapy.

64. An apparatus for predicting a quantitative probability of disease recurrence in a patient with prostatic cancer following an identified therapy, wherein the apparatus comprises:

a correlation of factors determined for each of a plurality of persons previously diagnosed with prostatic cancer and having been treated by said identified therapy with incidence of recurrence of prostatic cancer for each person of said plurality of persons, wherein said selected set of factors comprises two or more factors selected from the group consisting of pretreatment PSA level, combined Gleason grade, specimen Gleason sum, clinical stage, surgical margin status, prostatic capsular invasion maximum cancer length in a core, total length of cancer in the biopsy cores, percent of cores positive level, extraprostatic extension, level of extraprostatic extension, apoptotic index, percent of cancer in one or more cores, percent of high grade cancer in one or more cores, total tumor volume, zone of location of the cancer, presence of seminal vesicle invasion, type of seminal vesicle invasion, p53, Ki-67, p27, DNA ploidy status, lymph node status, and lymphovascular invasion; and a means for comparing an identical set of factors determined from the patient diagnosed as having prostatic cancer to the correlation to predict the quantitative probability of recurrence of prostatic cancer in the patient following said identified therapy.

* * * * *